United States Patent
Faltys et al.

(10) Patent No.: US 6,308,101 B1
(45) Date of Patent: Oct. 23, 2001

(54) FULLY IMPLANTABLE COCHLEAR IMPLANT SYSTEM

(75) Inventors: Michael A. Faltys, Northridge, CA (US); Janusz A. Kuzma, Englewood, CO (US); John C. Gord, Venice, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/404,966

(22) Filed: Sep. 24, 1999

Related U.S. Application Data

(63) Continuation-in-part of application No. 09/126,615, filed on Jul. 31, 1998, now Pat. No. 6,067,474.
(60) Provisional application No. 60/111,103, filed on Dec. 7, 1998.

(51) Int. Cl.[7] ....................................... A61N 1/36
(52) U.S. Cl. ............................................... 607/57
(58) Field of Search .................... 607/55, 56, 57

(56) References Cited

U.S. PATENT DOCUMENTS

| | | | |
|---|---|---|---|
| 3,942,535 | 3/1976 | Schulman | 128/419 |
| 4,006,748 | 2/1977 | Schulman | 128/419 |
| 4,134,408 | 1/1979 | Brownlee et al. | 128/419 |
| 4,495,917 | 1/1985 | Byers | 128/419 |
| 4,516,820 | 5/1985 | Kuzma | 339/48 |
| 4,819,647 | 4/1989 | Byers et al. | 138/642 |
| 4,991,582 | 2/1991 | Byers et al. | 128/419 |
| 5,314,451 | 5/1994 | Mulier | 607/33 |
| 5,314,457 | 5/1994 | Jeutter et al. | 607/116 |
| 5,411,537 | 5/1995 | Munshi et al. | 607/33 |
| 5,411,538 | 5/1995 | Lin | 607/33 |
| 5,601,617 | 2/1997 | Loeb et al. | 607/56 |
| 5,603,726 | 2/1997 | Schulman | 607/57 |
| 5,626,629 | 5/1997 | Faltys et al. | 607/57 |
| 5,881,158 | 3/1999 | Lesinski et al. | 381/174 |

FOREIGN PATENT DOCUMENTS

| | | |
|---|---|---|
| 1197468 | 9/1968 | (DE) . |
| 0499939 | 8/1992 | (EP) . |
| 9837926 | 2/1998 | (WO) . |

*Primary Examiner*—Scott M. Getzow
(74) *Attorney, Agent, or Firm*—Bryant R. Gold

(57) ABSTRACT

A fully implantable cochlear implant system (170) and method includes an implantable cochlear stimulator (ICS) unit (212) that is connected to an implantable speech processor (ISP) unit (210). Both the ISP unit and the ICS unit reside in separate, hermetically-sealed, cases. The ICS unit has a coil (220) permanently connected thereto through which magnetic or inductive coupling may occur with a similar coil located externally during recharging, programming, or externally-controlled modes of operation. The ICS unit further has a cochlear electrode array (114) permanently connected thereto via a first multi-conductor cable (116). The ICS unit 212 also has a second multi-conductor cable (222) attached thereto, which second cable contains no more than five conductors. The second cable is detachably connected to the ISP unit via a connector (224) located on the case of the ISP unit. The ISP unit includes an implantable subcutaneous microphone (218) as an integral part thereof, and further includes ISP circuitry (214) and a replenishable power source (216), e.g., a rechargeable battery.

20 Claims, 13 Drawing Sheets

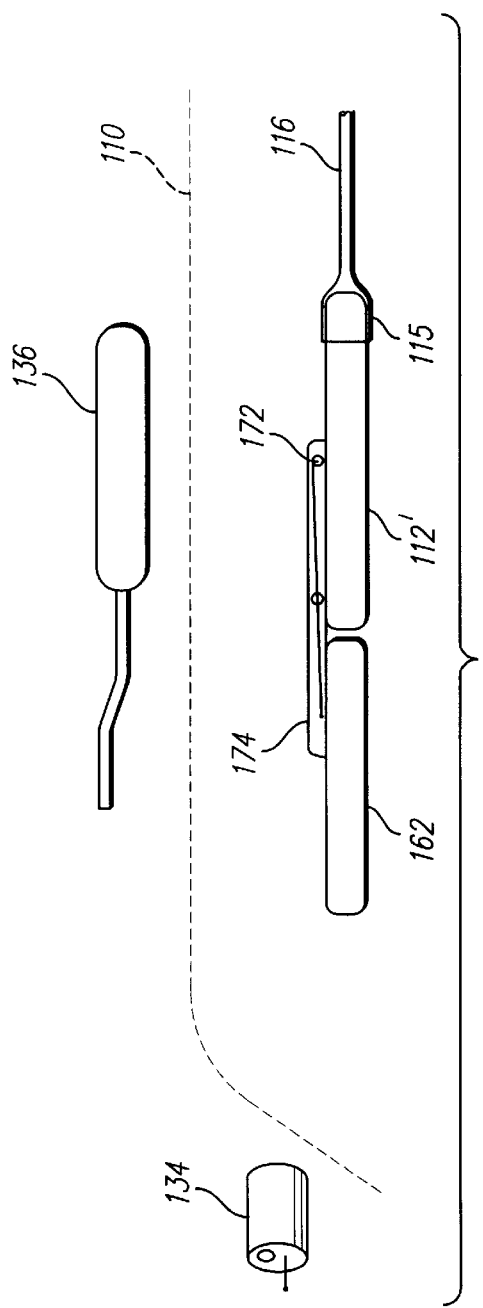
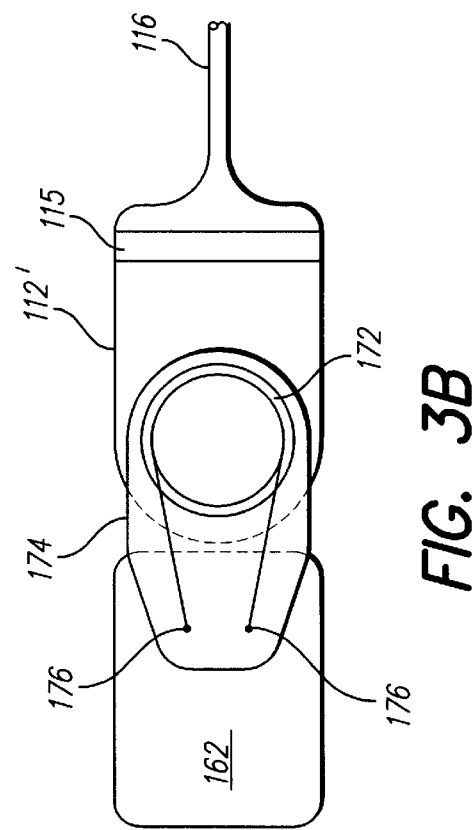
FIG. 3A
FIG. 3B

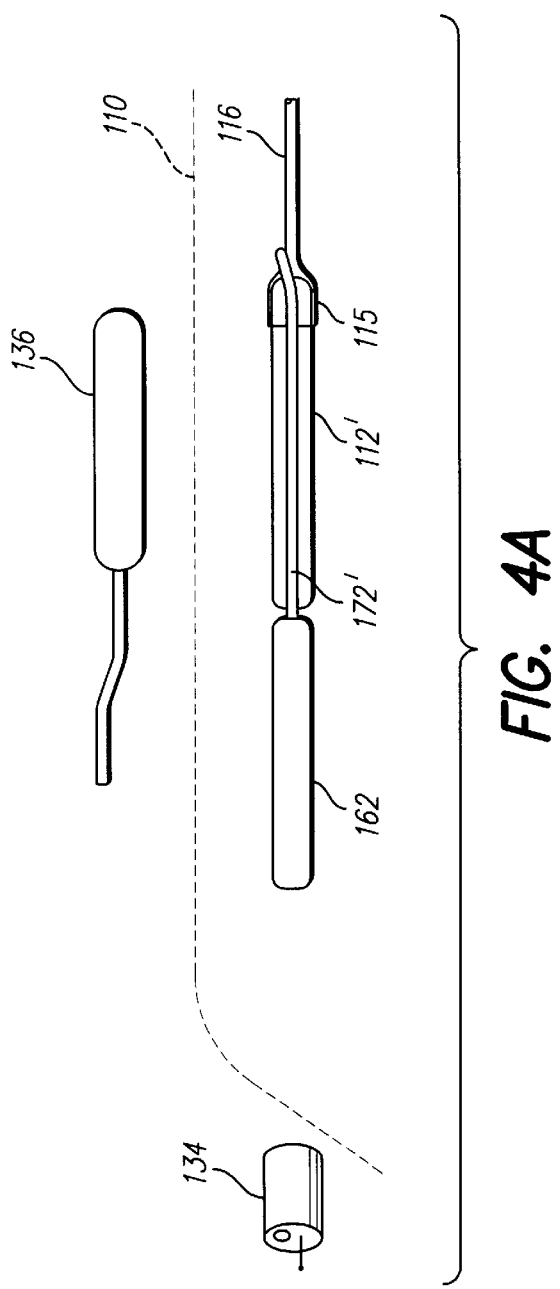
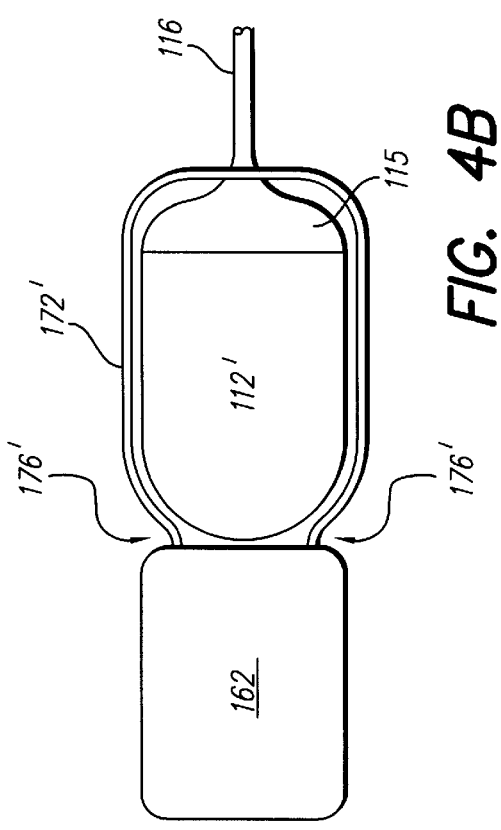
FIG. 4A
FIG. 4B

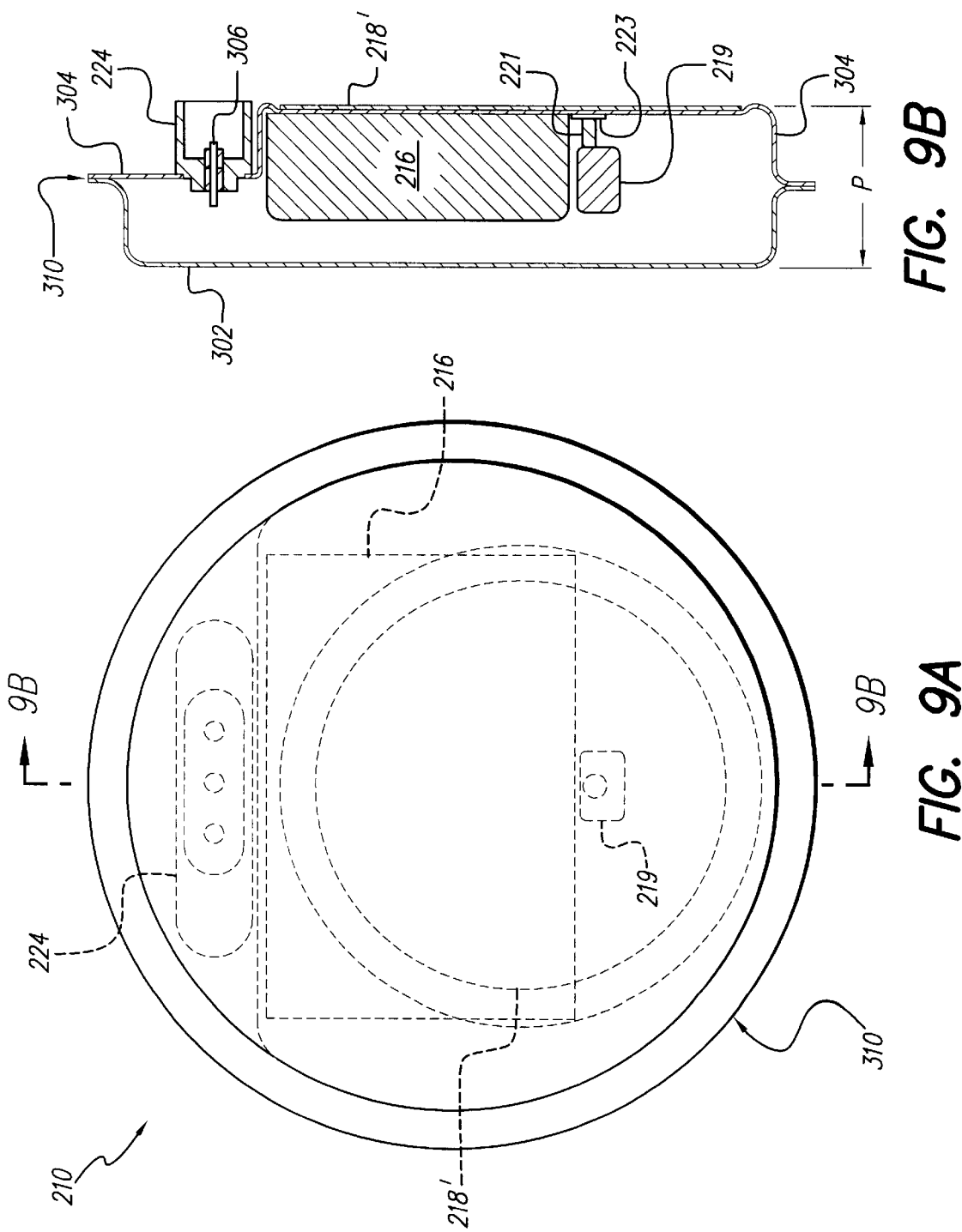

FULLY IMPLANTABLE COCHLEAR IMPLANT SYSTEM

This application is a continuation-in-part (CIP) of U.S. patent application Ser. No. 09/126,615, filed Jul. 31, 1998, now U.S. Pat. No. 6,067,474, which patent is incorporated herein by reference. This application further claims the benefit of U.S. Provisional Application Ser. No. 60/111,103, filed Dec. 7, 1998, which application is likewise incorporated herein by reference.

BACKGROUND OF THE INVENTION

The present invention relates to implantable devices, and more particularly, to a fully implantable device or system for stimulating or sensing within living tissue wherein the implantable device has a rechargeable battery or other replenishable power source. One aspect of the invention relates to partitioning the circuit functions within the implantable system to allow upgrading the circuit functions and/or to permit existing partially implantable systems (having both implanted and external, or non-implanted, components) to be converted to fully implantable systems; and/or to allow fully implantable systems to also function as a partially implantable system.

Presently available implantable stimulation devices, such as a cochlear implant device or a neural stimulator, typically have an implanted unit, an external ac coil, and an external belt-mounted control unit and power source. The external control unit and power source includes a suitable control processor and other circuitry that generates and sends the appropriate command and power signals to the implanted unit to enable it to carry out its intended function. The external control unit and power source is powered by a battery that supplies electrical power through the ac coil to the implanted unit via inductive coupling for providing power for any necessary signal processing and control circuitry and for electrically stimulating select nerves or muscles. Efficient power transmission through a patient's skin from the external unit to the implanted unit via inductive coupling requires constant close alignment between the two units.

Rechargeable implantable sensing and/or stimulation devices (e.g., heart pacemakers) are relatively bulky devices (e.g., 3 inches×2 inches×0.5 inches) and are quite heavy. Further, these rechargeable implantable devices require a substantial amount of charging time each week.

Accordingly, there exists a need for a small lightweight implantable device that does not require constant external power and that includes a long-lasting internal battery that may be recharged within a relatively short time period.

Further, there exists a need, should the battery within such a small, lightweight implantable device malfunction, or should the user desire to not use the internal battery for certain time periods, to still be able to provide power to the device, e.g., from an external power source, so that the device can continue to operate and provide its intended function, e.g., sensing and/or stimulating, to the patient, without having to implant a new device in the patient. Further, there exists a need for a fast, simple method for the battery module to be replaced during surgery, should replacement be necessary or desired.

Moreover, there are many patients who have received an implant system, e.g., a cochlear implant system of the type described in U.S. Pat. No. 5,603,726, incorporated herein by reference, which system includes both an implantable cochlear stimulator (ICS) attached to an electrode array that is inserted inside of the cochlea, and an external (non-implanted) battery, speech processor and headpiece. The speech processor (SP) and battery are housed within a wearable unit that is worn or carried by the patient, e.g., on a belt pack. The headpiece includes the external ac coil, a magnet, and a microphone. It is connected to the wearable unit via a cable. In use, the headpiece is positioned next to the external skin of the patient in close proximity to the ICS so as to provide efficient inductive coupling thereto. The magnet properly positions and holds the headpiece against the ICS implant location. Many of the patients who have and use the existing ICS system could greatly benefit from a fully implantable system, i.e., a system that eliminates the need for constantly wearing and/or carrying the external components of the system.

SUMMARY OF THE INVENTION

The present invention addresses the above and other needs by providing a fully implantable cochlear implant system having a rechargeable power source. In some embodiments, the rechargeable device of the invention may be used to upgrade the ICS portion of existing implant systems to fully implantable systems. The device may be recharged at a relatively fast rate thus minimizing disruptions to a patient's lifestyle. Once charged or recharged, the device may be used to power various implant configurations, including a fully implantable single unit, a wired system, or a proximity system.

Additionally, as a backup option, or for diagnostic purposes, the rechargeable device may be continuously powered from a small, lightweight external unit, if necessary or desirable. Thus, in the event the internal (implanted) battery within the device malfunctions, or for whatever reason cannot be used, or the user or clinician (or other medical personnel) does not want to use it, it is still possible, through use of the lightweight external device, to provide operating power to the implantable device so that it may continue to provide its intended function (e.g., stimulating and/or sensing). Advantageously, by having such a backup option available, the patient may delay indefinitely battery-replacement and/or corrective surgery.

One embodiment of the invention, hereafter referred to as the "single unit" embodiment, resides in an implantable device having a case, a coil, electronic circuitry, and a rechargeable battery. The case forms a substantially hermetic housing and the coil surrounds the case to enclose a relatively large area and generates electrical power in the presence of externally induced ac magnetic fields passing through the coil's enclosed area. The rechargeable battery and electronic circuitry are housed within the case.

Another embodiment of the invention, hereafter referred to as the "wired system" embodiment, resides in a fully implantable system that includes two implantable devices, each having its own case, jointed together by a detachable cable. A first of the implantable devices houses electronic circuitry for performing a desired function, e.g., stimulation of tissue. A second of the implantable devices houses a rechargeable battery or other replenishable power source, and may also include additional circuitry, e.g., to perform signal processing. The second device provides operating power for the first implantable device. Appropriate switching circuitry is included with the battery in the second device to convert the dc power of the battery to ac power for transmission to the first device. This ac power may be modulated, as desired, to also transmit information, e.g., control signals, from the second device to the first device. Thus, only ac power passes through the connecting cable.

In a preferred implementation of the "wired System" embodiment, there is provided a fully implantable cochlear implant system that includes an implantable cochlear stimulator (ICS) joined to an implantable speech processor (ISP) by way of a detachable cable. The ICS includes a cochlear electrode array permanently attached thereto. Such cochlear electrode array has a plurality, e.g., sixteen, spaced-apart electrode contacts thereon. The electrode array is adapted to be fully inserted into the patient's cochlea, where electrical stimulation may be selectively applied for the purpose of directly stimulating the auditory nerve, thereby providing the patient with the sensation of hearing. Also permanently attached to the ICS is a coil, which coil may be coupled, e.g., inductively coupled, with an external coil in a headpiece during a recharging and/or a programming mode of operation. Finally, a cable, having only five conductors therein, is also permanently attached to the ICS. This cable has a connector plug on its other end adapted to mate with a matching connector socket on the ISP. The ISP includes an implantable microphone as an integral part thereof, a rechargeable battery, and speech processing and other circuitry for processing and powering the various circuits used within the implant system.

In use, the ICS and implantable electrode array of this "wired system" embodiment are implanted in the patient, with the coil of the ICS being positioned in a convenient location for inductive coupling with the coil of an external headpiece. The ISP is also implanted near the ICS, and the cable from the ICS is attached to the connector of the ISP, thereby "wiring" the two components (ICS and ISP) together. The battery in the ISP provides operating power for the circuits within both the ICS and ISP. As required, the battery may be recharged through the coil attached to the ICS. The microphone attached to the ISP senses acoustic sound waves. A second microphone, e.g., an auxiliary microphone, such as an in-the-ear canal microphone or a middle-ear microphone, may also be attached to the implant system. The speech processing circuitry processes the sensed sound waves and generates control signals, in accordance with a selected speech processing strategy, and sends the control signals to the ICS. The ICS generates stimulation pulses that are applied to the cochlea through designated ones of the plurality of electrode contacts as a function of the control signals received from the ISP. The ISP may be programmed, or adjusted, through the use of an external programmer coupled with the external headpiece. In one embodiment, an acoustic remote control may be used to program the ISP directly, e.g., through the implanted microphone, without the need to first establish coupling between the ICS coil and an external coil.

Should the battery within the ISP become depleted, the ICS may operate directly from an external speech processor and headpiece, as is presently done with most cochlear implant systems. Further, in the event the battery or circuitry within the ISP malfunctions, and needs to be replaced, e.g., the battery no longer accepts a charging current, it is possible to explant the malfunctioning ISP and replace it with a new ISP. Such replacement surgery is facilitated by the connector on the case of the ISP which allows the cable from the ICS to be detachably removed from the old ISP and reattached to the new ISP.

Yet a further embodiment of the invention, hereafter referred to as the "proximity system" embodiment, resides in a fully implantable system that includes first and second implantable devices. The first device houses electronic circuitry for performing a desired function. The second device houses a rechargeable battery or other replenishable power source, and may also include additional circuitry. There is no direct electrical or physical connection between the first and second devices through which power and/or control signals are communicated from one device to the other. That is, there is no detachable cable that connects the two devices together as is the case with the "wired system" embodiment. Rather, power and control signals are inductively (magnetically) coupled from the second device to the first device in the same manner as is used to couple power and control signals between an external unit and an implanted unit in existing systems. Thus, one use of this proximity system embodiment allows a second device, housing a rechargeable battery and other circuitry that has heretofore been included in an external device, to be implanted proximate an implant device of an existing system, thereby effectively upgrading the existing system to a fully implantable system.

The present invention also resides in a method for recharging a battery within an implant device, e.g., within a cochlear implant device, that involves inducing an ac current in a coil that encircles the implant device, or that is contained within the implant device, or that is attached with two or more wires to the implant device, rectifying the induced ac current to produce dc current, and charging the battery using the dc current until the battery's voltage reaches a predetermined battery charge voltage or a predetermined coulomb value. For maximum battery lifetime for a lithium ion battery, the battery is charged to a voltage of no more than about 4.0 volts and is discharged to a voltage of no less than about 3.0 volts.

Such method for recharging may also be used, in accordance with another embodiment of the invention, to provide backup operating power to the implant circuitry in the event the internal rechargeable battery malfunctions, or is not to be used. Such backup powering may be accomplished, for example, using the same or a similar, small, lightweight external device, that is used for battery charging. Advantageously, having the option of providing backup power in this manner affords the patient the ability to defer indefinitely corrective- and/or battery-replacement surgery.

The backup powering option also allows greater flexibility in how the implant stimulation device is used. For example, in a cochlear implant device, it may be advantageous to change the speech processing strategy that is used to control the stimulation of the auditory nerves in the cochlea. Such speech processing strategy, in the first instance, is programmed inside of the implantable device. Should a new speech processing strategy be desired, and in the event reprogramming of the speech processing strategy within the implantable device is not feasible or possible, then a small, lightweight, behind the ear unit could be worn by the patient that incorporates the new speech processing strategy, and powers and controls the implanted stimulation circuitry within the implantable device to apply the new stimulation strategy.

The invention further includes an implant system consisting of two packages. In one specific embodiment, the first package includes the coil, battery, battery charging and power regulation circuitry and some of the electronics circuitry (signal handing and processing circuitry) that may potentially need to be updated or upgraded in the future as new signal processing and data handling technologies evolve. The second package includes the wires going to the stimulation and sensing electrodes and devices, and the interface circuitry for stimulating and sensing, as well as other signal processing and conditioning circuits which are intimately associated with the stimulation and sensing functions performed within the second package, and which are not likely to change or need to be updated or upgraded as new technologies evolve. Thus, the first package is a package that can, if needed, be replaced or upgraded at a future time through minor replacement surgery. The second package is a package that, once implanted, should not ever need replacing or upgrading.

Also, in both the first and second packages, circuitry is included to permit capacitive coupled data transmission and reception circuits that are used to transfer data and power between the two packages. The packages can be connected with a detachable cable ("wired system") or can be coupled together through induction coupling ("proximity system"). In these systems, by way of example, data and power may be transferred between the two packages on two or three wires. In such coupled systems, power may be transferred via an ac carrier signal, and data may be transferred by modulating the carrier signal.

BRIEF DESCRIPTION OF THE DRAWINGS

The above and other aspects, features and advantages of the present invention will be more apparent from the following more particular description thereof, presented in conjunction with the following drawings wherein:

FIGS. 3A and 3B are a plan and profile (side) view, respectively, of one embodiment of a fully implantable, partitioned, proximity system made in accordance with the invention.

FIGS. 4A and 4B are similarly a plan and profile view, respectively, of another embodiment of a fully implantable, partitioned, proximity system.

FIGS. 9A and 9B are a plan and side cross-sectional view, respectively, showing the preferred mechanical packaging of the ISP used in the system shown in FIG. 6.

Corresponding reference characters indicate corresponding components throughout the several views of the drawings.

DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Overview

The present invention relates to a fully implantable device having a rechargeable battery (or other power source). In a preferred embodiment, the implantable device comprises a fully implantable cochlear implant system, and thus such a cochlear implant system is described herein. It is to be understood, however, that the present invention may also be used with other types of implantable systems, and is not intended to be limited to just a cochlear implant system. Any medical or other device or system which must be implanted in living tissue, or a similar environment, and which requires operating power from a replenishable power source, such as a rechargeable battery, and wherein the operating power must be coupled into the implantable device without a direct electrical connection, may benefit from the application and teachings of the present invention.

Figure 1A:
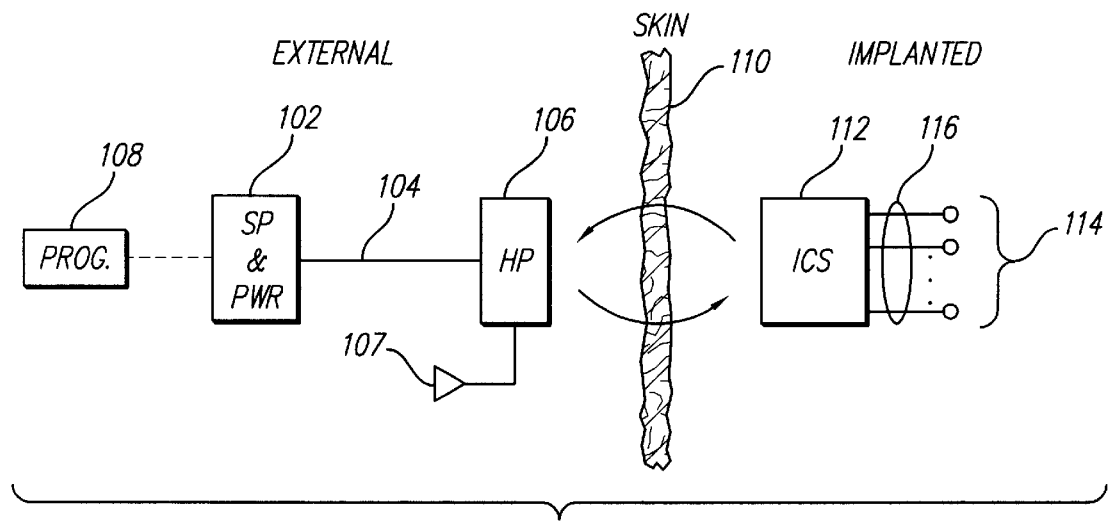
FIG. 1A illustrates a typical cochlear stimulation system as currently used by many patients, including an implantable cochlear stimulator (ICS) that is inductively coupled with an external headpiece (HP) connected with an external speech processor (SP) and power source.

To better understand and appreciate the present invention, it will be helpful to briefly review current or existing cochlear implant systems, which are representative of all tissue-stimulating systems. A representative cochlear stimulation system of the type currently used by many patients is fully described, e.g., in U.S. Pat. No. 5,603,726, previously referenced and incorporated herein by reference. As described in the '726 patent, and as illustrated in FIG. 1A, such existing system includes implanted and external components. The external components include a speech processor (SP), a power source (e.g., a replaceable battery), and a headpiece (HP) 106. The SP and power source are typically housed within a wearable unit 102 that is worn or carried by the patient. The wearable unit is electrically connected to the HP 106 via a cable 104. A microphone 107 is also included as part of the headpiece 106.

The implanted components include an implantable cochlear stimulator (ICS) 112 and an array of electrodes 114. The electrode array 114 is intended for implantation within the cochlea of the patient. The ICS 112 is implanted behind the ear, so as to reside near the scalp. The electrode array 114 is permanently connected to the ICS by way of a multi-conductor implantable cable 116.

Inside of the headpiece 106 is a coil that is used to inductively or magnetically couple a modulated ac carrier signal to a similar coil that is included within the ICS 112.

In order to achieve efficient coupling, without suffering significant losses in the signal energy, it is important that the external coil within the headpiece be properly aligned with the internal coil inside the ICS. To achieve proper alignment, a magnet is typically included within both the headpiece 106 and the ICS 112, and the resulting magnetic attraction between the two magnets not only aligns the coils, as desired, but also provides a holding force that maintains the headpiece 106 securely against the scalp or skin 110 of the patient.

In use, a carrier signal is generated by circuitry within the wearable unit 102 using energy derived from the power source within the speech processor unit 102. Such carrier signal, which is an ac signal, is conveyed over the cable to the headpiece 106 where it is inductively coupled to the coil within the ICS 112. There it is rectified and filtered and provides a dc power source for operation of the circuitry within the ICS 112. Sounds are sensed through the external microphone 107, amplified and processed by circuitry included within the speech processor unit 102, and converted to appropriate stimulation signals in accordance with a selected speech processing strategy by circuitry within the speech processor unit 102. These stimulation signals modulate the carrier signal that transfers power to the ICS 112. The ICS includes an appropriate demodulation circuit that recovers the stimulation signals from the modulated carrier and applies them to the electrodes within the electrode array 114, The stimulation signals identify which electrodes, or electrode pairs, are to be stimulated, and the intensity of the stimulation.

Some embodiments of the ICS 112, as indicated in the '726 patent, include a backtelemetry feature that allows data signals to be transmitted from the ICS 112 to the headpiece 106, and hence to the Speech Processor 102. Such backtelemetry data provides important feedback information to the speech processor regarding the operation of the ICS.

When adjustment or fitting or other diagnostic routines need to be carried out, an external programming unit 108 is detachably connected to the SP unit 102. Through use of the external programmer 108, a clinician, or other medical personnel, is able to select the best speech processing strategy for the patient, as well as set other variables associated with the stimulation process. See, e.g., U.S. Pat. No. 5,626,629, incorporated herein by reference, for a more detailed description of a representative fitting/diagnostic process.

Although the system shown in FIG. 1A has been of great value and benefit to many patients who could not otherwise experience the sensation of hearing, there are several drawbacks associated with use of the system. For example, the wearable unit 102 must be worn or carried by the patient, and the cable 104, which may be up to one meter long, must be routed from the unit 102 to the headpiece 106. Some patients find wearing the unit 102 to be inconvenient, and find the use of the headpiece 106, with its cable 104, to be unsightly and uncomfortable.

Figure 1B:
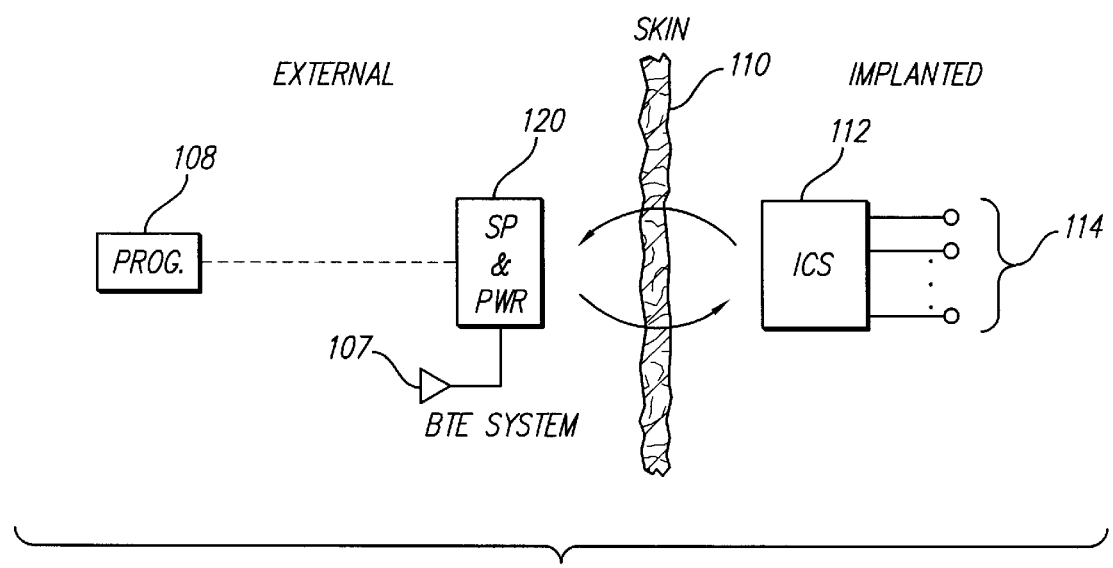
FIG. 1B illustrates a behind-the-ear (BTE) cochlear stimulation system that includes an implanted cochlear stimulator (ICS) and an external BTE unit that includes a power source, a speech processor and a microphone.

In order to eliminate the need for the cable 104, a behind-the-ear (BTE) unit 120 may be used, as illustrated in FIG. 1B. the BTE unit 120 includes everything that was previously included within the wearable unit 102, only in a much smaller volume. The BTE unit 120 thus includes a suitable power source, as well as circuitry for performing a desired speech processing function. With the BTE unit 120, there is thus no need for the cable 104, and the patient simply wears the BTE unit behind his or her ear, where it is hardly noticed, especially if the patient has hair to cover the BTE unit.

Advantageously, the batteries employed within the wearable unit 102 (FIG. 1A) or the BTE unit 120 (FIG. 1B) may be readily replaced when needed. Still, the BTE unit 120 may become uncomfortable to wear when worn for long periods of time, and must be removed at certain times, such as when swimming or bathing. Some patients would thus like the convenience of being able to hear at all times, including when swimming or bathing, and thus a fully implantable stimulation system is desired.

The present invention is directed to fully implantable devices and systems that employ a rechargeable battery or other replenishable power source. While it is known in the art to use an implantable stimulating device with a rechargeable battery, see, e.g, U.S. Pat. No. 3,942,535, such recharging systems require a bulky external recharging system, and are time consuming to use. In contrast, the present invention provides a rechargeable battery, and method of recharging the battery, that allows the recharge operation to occur quickly and conveniently, without significant impact on the patient's lifestyle.

The present invention also allows different implant configurations to be used as part of the fully implantable system, including the ability to use the ICS 112 of the prior systems in a fully implantable system.

Figure 1C:
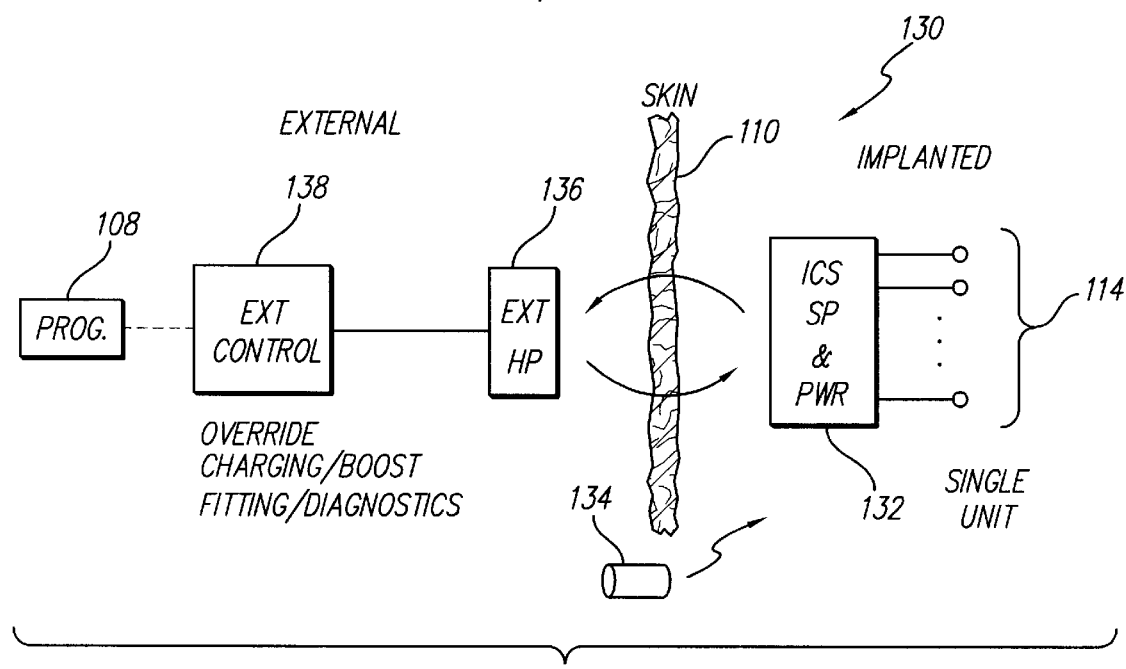
FIG. 1C shows one type of a single unit, fully implantable system made in accordance with the present invention.

A fully implantable single unit system 130 made in accordance with the invention is shown in FIG. 1C. As illustrated in FIG. 1C, such system 130 includes the ICS circuitry, the speech processor circuitry, and a power source, all housed within a single unit 132. An electrode array 114 is connected to the single unit 132 in conventional manner. For the embodiment shown in FIG. 1C, a microphone 134 is coupled via a telecoil link to the single unit 132. Such telecoil link powers the microphone circuits through magnetic coupling from the unit 132. Sounds sensed by the microphone 134 are transmitted to the unit 132 via an rf transmitter built-in to the microphone 134. (The transmission distance for such signal is very short, only a centimeter or two, so not much power is needed for such transmission.) Advantageously, such microphone 134 is inserted inside the ear canal so it is not visible externally.

Other types of microphones may also be used with the implant unit 132. For example, externally-generated sound waves may be sensed through the patient's skin and case of the single unit 132 at locations where the case shell is properly supported and of the proper thickness.

When the battery included within the single unit 132 needs to be recharged, which may only be a few minutes a day, or a few times during the week, an external headpiece 136 is placed adjacent the unit 132, and inductive coupling is used to transfer charging power to the unit's battery. The external headpiece, in turn, connects to an external control unit 138, which may, in turn, derive its power from replaceable batteries or from an ac power plug. When programming and/or diagnostic tests are needed, an external programmer 108 may be detachably connected to the external control unit 138.

The external control unit 138 is thus used to charge/recharge the battery within the implanted unit 132, as well as for other purposes. For example, the external control unit 138 may be used to override the internal speech processor with an external speech processor, e.g., a speech processor included within the external programmer 108. Further, the external control unit 138 may be used to boost the power provided by the internal battery. The external control unit 138 may also be used for programming the implant device 132, e.g., fitting the ICS after implant or adjusting the stimulation parameters of the fully implantable unit 132, as well as for diagnostic purposes.

For the embodiment 130 shown in FIG. 1C, as well as for the other embodiments shown in FIGS. 1D, 1E and 1F, discussed below, it is to be understood that backtelemetry may be employed to allow data signals to be sent from the implanted unit to the external headpiece 136, and hence to the external control unit 138.

Figure 1D:
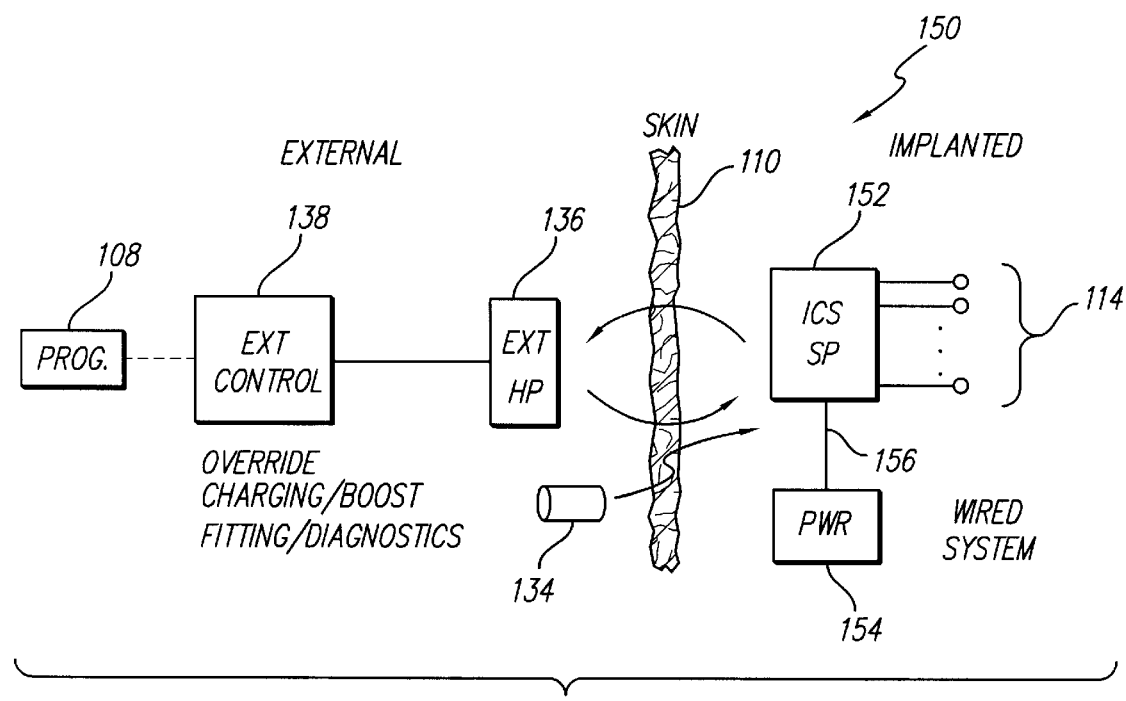
FIG. 1D shows one type of a fully implantable, partitioned, wired system in accordance with the invention.

Turning next to FIG. 1D, a "wired system" embodiment 150 of the invention is depicted. In such wired system 150, at least two separate implantable units 152 and 154 are employed and the circuits of the system are partitioned between the two units. In a first unit 152, for example, speech processor (SP) and ICS circuitry are housed, and such unit is permanently connected to an electrode array 114. In a second unit 154, a battery, or other suitable power source, is housed. The second unit 154 is electrically connected to the first unit 152 via a detachable cable 156. In a preferred embodiment, only ac power is coupled from the power unit 154 to the SP/ICS unit 152, thereby preventing any possibility that a dc current might flow through the tissue through which the cable is routed. This is important because a dc current could cause damage to the tissue, whereas an ac current will not. Also, because the cable is not hermetically insulated from the surrounding tissue, it is very possible that minor leakage current could flow through the tissue if it carried dc currents.

The second unit 154 includes appropriate switching circuitry that converts the dc power associated with the battery (or other power storage element) therein to an ac signal for coupling to the first unit 152. Also, appropriate circuitry is employed to allow ac power induced into the unit 152 from the external headpiece 136 to be directed to the battery in the unit 154 in order to charge the battery.

Although the preferred power source for use within the fully implantable systems described herein is a rechargeable battery, it is to be understood that other power sources may also be employed. For example, an ultracapacitor (also known as a supercapacitor) may be used. An ultracapacitor, like a conventional capacitor, allows an electric charge (voltage potential) to be stored therein. Unlike a regular capacitor, the energy density of the ultracapacitor is orders of magnitude greater than the energy density of a normal capacitor, thereby allowing a great amount of energy to be stored in the ultracapacitor. This stored energy may then be withdrawn from the ultracapacitor for subsequent use. Thus, for this type of application, where recharging must occur on a regular basis, and when appropriate discharge circuits are employed to control the rate of discharge or energy withdrawal, the ultracapacitor provides a viable alternative to a rechargeable battery for use within the implantable system.

A suitable microphone, e.g., a complete-in-cannel (CIC) microphone 134 of the type described previously, is used to sense sounds and couple signals representative of such sounds to the speech processor (SP) circuits within its respective implantable portion. Alternatively, other microphones, e.g., an implantable microphone, may be used.

It should be noted that the partitioning illustrated in FIG. 1D, which shows that the ICS and SP circuitry are included within the first implantable unit 152, and which shows that the power source, e.g., rechargeable battery, is included within the second implantable unit 154, is only exemplary. For some embodiments, for example, the SP circuitry may be included within the second implantable unit 154, leaving only the ICS circuitry within the first implantable unit 152. Such an embodiment, for purposes of the present application, is preferred, and is illustrated in FIG. 1F below, and is further described in more detail in conjunction with the description of FIG. 6 through FIG. 10B.

Figure 1E:
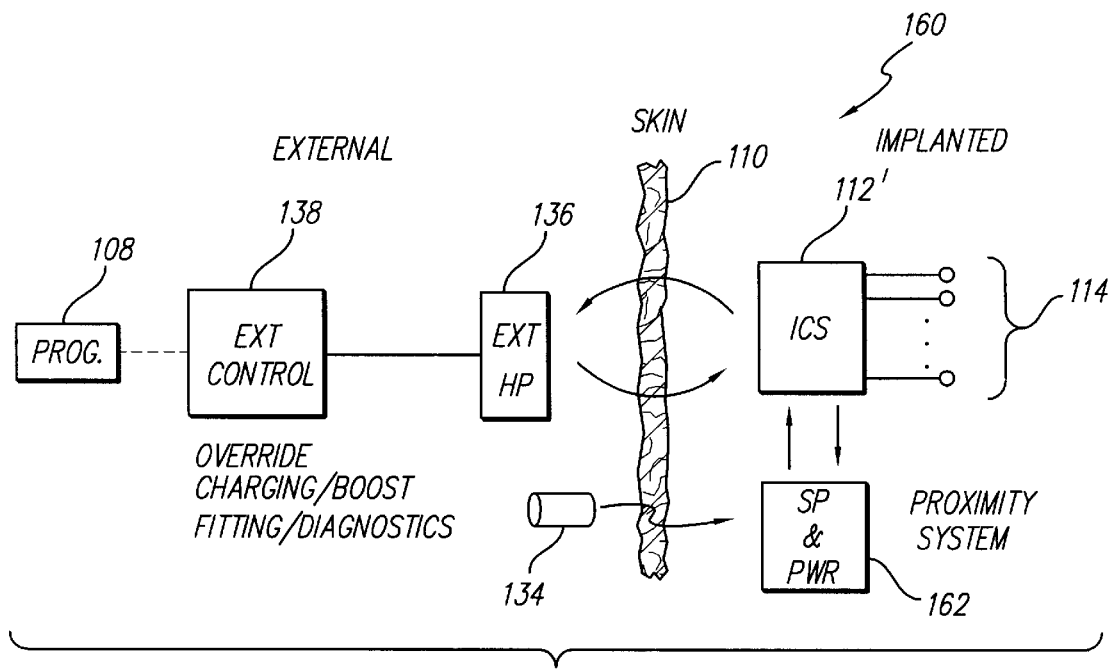
FIG. 1E shows one type of a fully implantable, partitioned, proximity system in accordance with the invention.
Figure 1F:
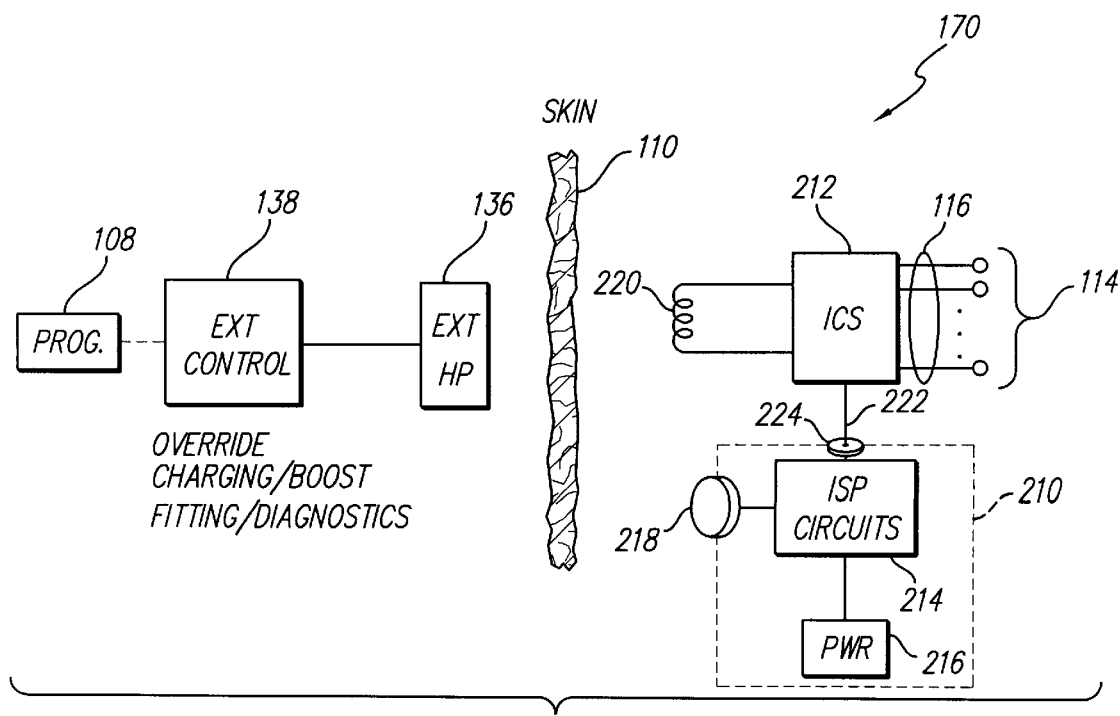
FIG. 1F shows a preferred type of fully implantable, partitioned, wired cochlear implant system in accordance with the invention.

The advantage of the wired system 150 shown in FIG. 1D or FIG. 1F is that a fully implantable system is provided wherein one of the two implantable units, e.g., the power unit 154, may be replaced, if necessary, through only minor surgery. As indicated, the cable 156 that connects the second unit 154 to the first unit 152 is detachable. The implantable connector that connects the cable 156 to the unit 154, may be of any suitable type, e.g., of the type commonly used with implantable pacemakers, or of the pressure type shown in U.S. Pat. No. 4,516,820 (Kuzma), incorporated herein by reference, or of the type shown in U.S. Pat. No. 4,495,917 (Byers), also incorporated herein by reference. Alternatively, a connector of the type disclosed in U.S. patent application Ser. No. 09/239,926, filed Jan. 28, 1999, now U.S. Patent 6,198,969, incorporated herein by reference, may be used.

Preferably, a connector of the type shown in U.S. Provisional Patent Application Ser. No. 60/111,103, filed Dec. 7, 1998, is used to detachably couple the cable 156 to the unit 154. A copy of this provisional application is incorporated herein by reference. This provisional application has now been converted to a non-provisional application Ser. No. 09/455,046, filed Dec. 26, 1999.

The external headpiece 136 and external control unit 138, and programmer 108, may be used with the wired system embodiment 150 shown in FIG. 1D in the same manner as these components are used with the single unit embodiment 130 shown in FIG. 1C.

Turning next to FIG. 1E, a partitioned proximity system 160 is shown that is similar to the wired system 150 shown in FIG. 1D, but without the use of a connecting cable 156 between the two units. As seen in FIG. 1E, a first implantable unit 112' comprises an ICS with an electrode array 114 connected thereto. An advantage of the proximity system 160 is that the first implantable unit 112' may be substantially the same as, or identical to, that of the ICS 112 used in existing cochlear stimulation systems (see FIG. 1A or FIG. 1B). This allows existing stimulation systems having an ICS 112 to be upgraded to a fully implantable system as shown in FIG. 1E. A second implantable unit 162 includes speech processor (SP) circuits and a power source, e.g., a rechargeable battery. The second unit 162 is implanted so as to be in close proximity to the first unit 112'. A coil associated with the second unit 162 is aligned with the coil included within the ICS 112'. This allows inductive coupling to occur between the implantable units 112' and 162 in the same manner as occurs between the BTE unit 120 and the ICS 112 shown in FIG. 1B, or between the headpiece 106 and the ICS 112 shown in FIG. 1A.

A suitable microphone, e.g., an complete-in-cannel (CIC) microphone 134 of the type described previously, or another type of microphone, e.g., an implantable microphone, is used to sense sounds (pressure waves) and couple electrical signals representative of such sounds to the speech processor (SP) circuits within the implantable portion 162.

The external headpiece 136 and external control unit 138, and programmer 108, may be used with the partitioned proximity system embodiment 160 shown in FIG. 1E in the same manner as used with the single unit embodiment 130 shown in FIG. 1C and the partitioned wired system embodiment 150 shown in FIG. 1D.

By using the system shown in FIG. 1E, it is seen that the following advantages are achieved: (1) older implants, i.e., existing ICS units 112, may be upgraded to fully implantable systems without replacing the implant unit 112 and electrode 114; (2) implantable systems may be upgraded with improved battery (or other power source) technology and lower-power more-sophisticated SP circuits, as such become available, with only minor surgery for the patient; (3) batteries can be replaced with only minor surgery, as required; and (4) charging, override, power boost, fitting and diagnostics may be performed by simply overriding the implanted SP circuits with an external speech processor.

Next, with reference to FIG. 1F, a preferred, partitioned, "wired" cochlear implant system 170 is illustrated. The external headpiece 136 and external control unit 138, and programmer 108, may be used with the partitioned wired system 170 shown in FIG. 1F in the same manner as used with the single unit embodiment 130 shown in FIG. 1C, the partitioned wired system embodiment 150 shown in FIG. 1D and the partitioned proximity system 160 shown in FIG. 1E. As seen in FIG. 1F, the cochlear system 170 includes an implantable cochlear stimulator (ICS) unit 212 that is "wired" to an implantable speech processor (ISP) unit 210. The ICS unit 212 has a coil 220 permanently connected thereto through which magnetic or inductive coupling may occur with a similar coil located in the external headpiece 136 during recharging, programming, or externally-controlled modes of operation. The ICS unit 212 further has an electrode array 114 permanently connected thereto via a multi-conductor cable 116. The ICS unit 212 also has a multi-conductor cable 222 attached thereto. In a preferred embodiment, this cable 222 contains five conductors. The cable 222 is detachably connected to the ISP unit 210 via a connector 224 located on the case of the ISP unit 210. The ISP unit 210 includes an implantable microphone 218 as an integral part thereof, and further includes ISP circuitry 214 and a replenishable power source 216, e.g., a rechargeable battery. The advantages of the wired system 170 shown in FIG. 1F are as previously mentioned—primarily a fully implantable system is provided wherein one of the two implantable units, e.g., the ISP unit 210, may be replaced, if necessary, through only minor surgery; and the ICS unit 212 may function, if desired, through use of an external control unit 138 and headpiece 136. As indicated, the cable 222 that connects the ICS unit 212 to the ISP unit 210 is detachable.

Improved Battery Charging

The techniques employed to make the charging of the rechargeable battery or other replenishable power source more efficient are more fully described in parent patent application Ser. No. 09/126,615, filed Jul. 31, 1998, now U.S. Pat. No. 6,067,474, previously incorporated herein by reference, and will not be repeated herein. Suffice it to say that such techniques, when used, seek to reduce eddy currents induced in the implant's conductive structures and current paths. If the implant's temperature rises too high, damage to the surrounding tissue may result. The implant devices of the present invention are configured to reduce the amount of heat generated during the battery's charging time and to extend the battery's lifetime.

Figure 2:
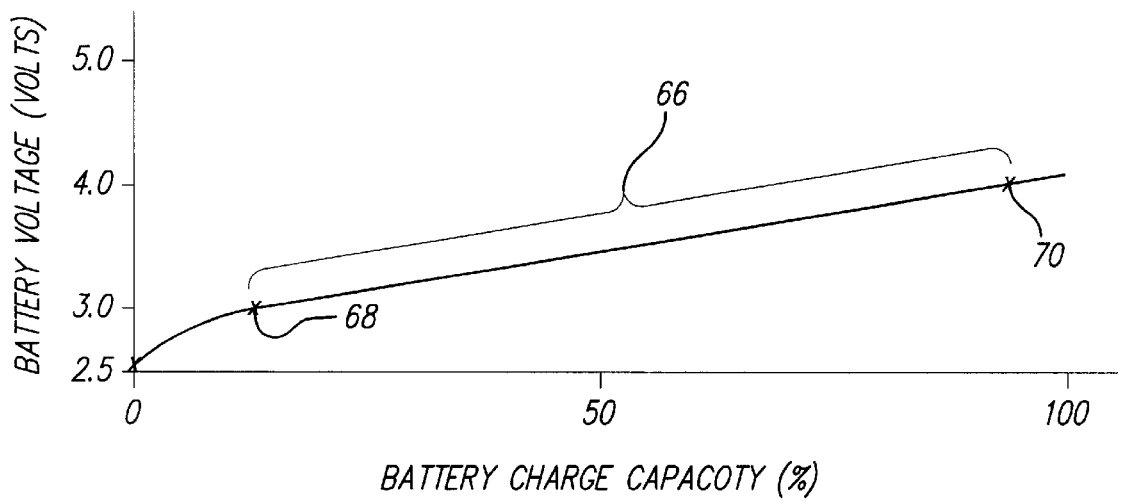
FIG. 2 is a graph of battery voltage verses battery charge capacity.

In this regard, it is also important to note that the rechargeable battery's lifetime may be improved significantly by using it only in low stress regions 66 of its operational range, as shown in FIG. 2. More specifically, rechargeable battery cycle lifetime is based on the number of full discharges and charges or cycles that the battery can perform while maintaining its power delivery specifications. For a lithium ion battery, a battery voltage of 2.55 volts indicates a fully discharged battery and a battery voltage of 4.1 volts indicates fully charged battery charge. However, fully discharging or fully charging the battery "stresses" the battery and limits its lifetime. Operating the battery within a relatively "low-stress" region 66 of the battery's operational range thus significantly extends the battery's lifetime. For example, recharging the battery when its voltage drops to 3.0 volts (point 68 on the battery charging curve of FIG. 2) and charging it to no more than 4.0 volts (point 70 on the battery charging curve) allows the battery to operate mainly within the low-stress regions of its operational range. Thus, even though the battery may have sufficient capacity to operate for two days between recharging, battery lifetime may be extended by daily or twice daily partial battery recharging.

Alternatively, a coulomb counter may be used instead of, or in addition to, a voltage level meter to monitor the battery's charge level. The coulomb counter may also indicate the battery's power efficiency.

Fully Implantable Systems

Fully implantable systems made in accordance with the present invention have been described previously in connection with FIGS. 1C, 1D, 1E and 1F.

FIG. 3A shows a plan view, and FIG. 3B a side view, of one type of partitioned fully implantable proximity system 160 (FIG. 1E). In the embodiment shown in FIGS. 3A and 3B, an ICS 112' is positioned proximate an implantable SP/PWR unit 162. The ICS 112' is housed within a ceramic case of the type described in U.S. Pat. No. 4,991,582, incorporated herein by reference. Ceramic, or an equivalent material, is preferably used for the case material to facilitate magnetic coupling through the case. A metal header 115 is hermetically sealed to one end of the ceramic case. Electrical feedthroughs positioned in the header 115 provide an hermetic electrical connection of the individual conductors of the cable 116 (which goes to the electrode array 114, not shown in FIGS. 3A or 3B) to the electrical circuitry housed within the ICS 112'.

The SP/PWR unit 162 is housed in a case which may be metallic, e.g., titanium, stainless steel, or similar material that is compatible with body tissues. Two electrical feedthroughs 176 pass through one side of the case and attach to a coil 172. The coil is aligned with and positioned over the coil that is included within the ICS 112'. The coil may be embedded within a suitable material, such as an encasing mold 174 made of silicone rubber or other suitable material, which mold is formed so as to adhere to the sides of the SP/PWR unit 162 and the ICS 112'. A complete-in-canal (CIC) microphone 134 is placed in the ear canal adjacent the implant location of the ICS 112' and SP/PWR unit 162. A telecoil link couples magnetic energy into the microphone which it uses as power to power its internal circuits. Sound (pressure waves) sensed by the microphone are converted to electrical signals which are transmitted via an RF transmitter or other suitable link the short distance to the SP/PWR unit 162. As needed, an external headpiece 136 (connected to an external programmer, not shown in FIG. 3B) may be positioned over the implant devices, on the outer side of the patient's skin 110, so as to override the internal speech processor, provide a charging or boosting current for the implant device, or to perform fitting and/or diagnostic functions.

An alternative embodiment of the fully implantable partitioned proximity system 160 (FIG. 1E) is illustrated in FIGS. 4A and 4B. FIG. 4A is a plan view of such embodiment, and FIG. 4B is a side or profile view. As seen in these figures, the ICS 112' and the SP/PWR unit 162 are placed side-by-side, proximate each other. Each unit has approximately the same thickness. Electrical feedthroughs 176' at one end of the SP/PWR unit 162 provide electrical connection for the coil 172'. Preferably, the coil 172' includes one or more turns of a suitable wire, e.g., a wire made from one of the noble metals, held together to form a cable or held within a suitable flexible conduit.

During the implant operation, the ICS 112' is implanted in conventional manner, and the SP/PWR unit is likewise implanted proximate thereto. The surgeon places the coil 172' so that it encircles the ICS 112', with the cable passing over the fantail portion the electrode array cable 116. The surgeon who performs the implant operation may suture the coil in place, as needed. A microphone 134, and an external headpiece 136 are used with the SP/PWR unit 162 and ICS 112' as described previously.

Figure 5:
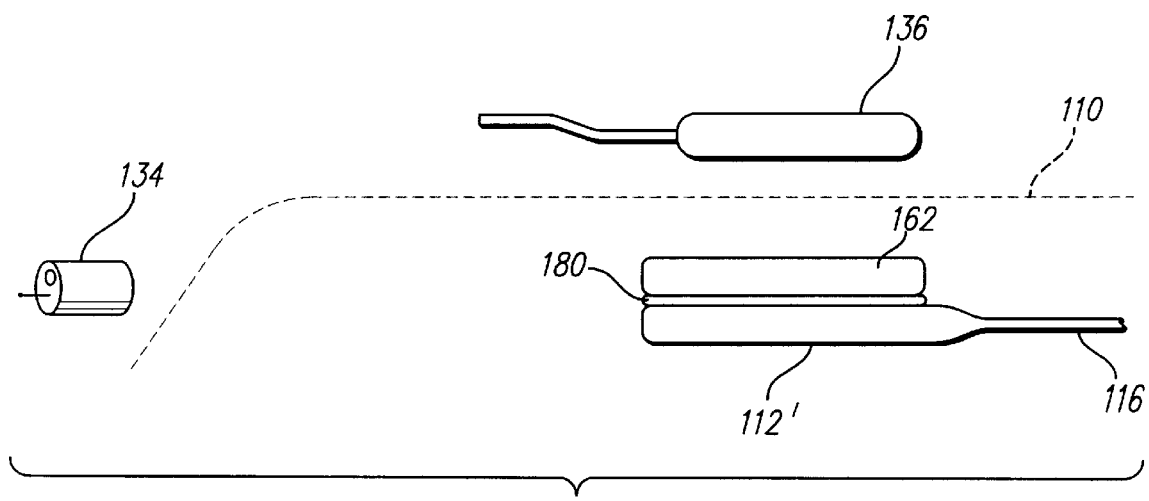
FIG. 5 is a profile view of yet another embodiment of a partitioned proximity system.

Yet a further embodiment of the fully implantable partitioned proximity system 160 (FIG. 1E) is illustrated in FIG. 5. As shown in FIG. 5, which shows a profile view of such embodiment, an ICS 112' and an SP/PWR unit 162 are stacked on top of each other. For the embodiment of FIG. 5, it is preferred that the SP/PWR unit 162 also have a ceramic case, like the ICS 112', or otherwise be designed so that magnetic signals may pass therethrough without significant degradation. An advantage of the embodiment of FIG. 5 is that the SP/PWR unit 162 need not employ any hermetic feedthroughs. Rather, it may comprise a sealed hermetic unit having its coil inside of its case. A disadvantage of the embodiment of FIG. 5 is that the combined stack of the ICS 112' and the SP/PWR unit 162 are at least twice as thick as are the side-by-side embodiments, thereby requiring a deeper pocket to be formed in the patients tissue during implant, and perhaps resulting in a small bulge or bump on the patient's skin at the implant site.

During the implant operation for the embodiment of FIG. 5, the case of the SP/PWR unit 162 is simply placed over the ICS 112' so as to align its coil with the coil of the ICS 112'. If desired, a thin ferrite sheet 180, or a sheet made from other suitable low magnetic reluctance material, coated with a suitable protective, biocompatible material, may be inserted between the outer walls of the two units in order to help confine and focus the magnetic field associated with the inductive coupling to the desired area.

Figure 6:
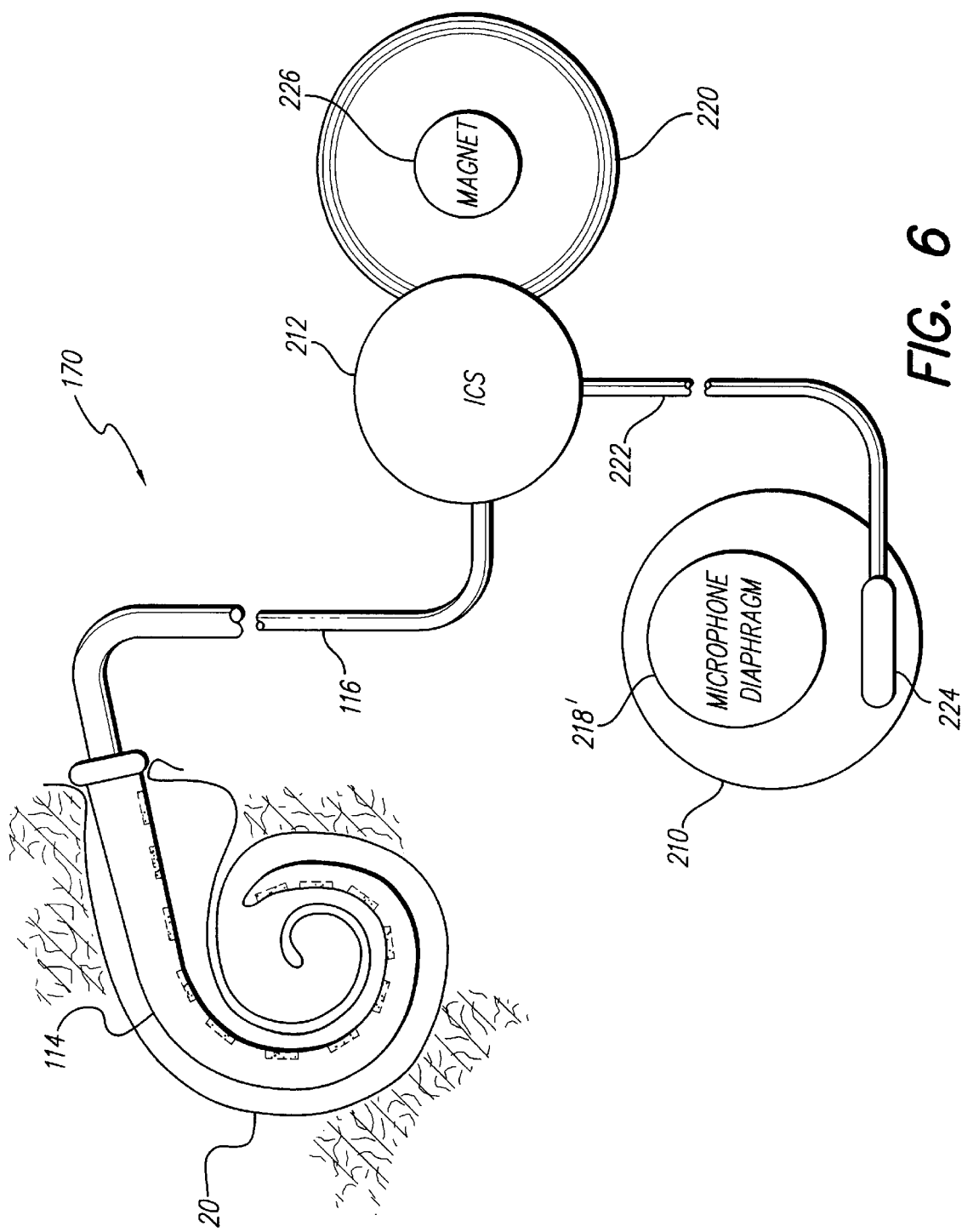
FIG. 6 is a schematic diagram showing a preferred, partitioned, wired, cochlear implant system in accordance with the invention, and shows the electrode array of such system inserted into the cochlea.

Turning next to FIG. 6, a schematic representation of the fully implantable, partitioned, "wired" cochlear implant system 170 of FIG. 1F is illustrated. That which is shown in FIG. 6 differs from that shown in FIG. 1F only in that the ICS unit 212, including its coil 220, and the ISP unit 210, including its connector 224 and microphone diaphragm 218' are shown having the approximate shape and relative size as they have in a preferred cochlear implant system. Also included in FIG. 6 (and not shown in FIG. 1F) is a permanent magnet 226 that is positioned in the center of the coil 220. It is this magnet 226 that holds the external headpiece 136 (FIG. 1F) against the skin and in alignment with the coil 220 when the external headpiece is used. Further shown in FIG. 6 (and not shown in FIG. 1F) is an actual cochlear electrode array 114 inserted into a cochlea 20. (It is noted that the electrode array 114 and cochlea 20 are not drawn to scale, but are shown much larger relative to the size of the ICS 212 and ISP 210 than in would exist in actuality.)

As shown in FIG. 6, the cochlear implant system 170 includes an implantable cochlear stimulator (ICS) unit 212 that is "wired" to an implantable speech processor (ISP) unit 210. The ICS unit 212 has a coil 220 permanently connected thereto through which magnetic or inductive coupling may occur with a similar coil located in the external headpiece 136 during recharging, programming, or externally-controlled modes of operation. A permanent magnet 226 is mounted in the center of the wire coil 220 to aid in holding the headpiece in alignment with the coil when the headpiece is used. The ICS unit 212 further has an electrode array 114 permanently connected thereto via a multi-conductor cable 116. The electrode array 114 is inserted deep into the cochlea 20, as is known in the cochlear implant art.

The ICS unit 212 also has a multi-conductor cable 222 attached thereto. In a preferred embodiment, this cable 222 contains five conductors, each of which passes through the hermetically sealed case of the ICS unit 212 via respective feedthrough connectors in order to make electrical connection with the electrical circuitry located inside of the ICS case. The cable 222 is detachably connected to the ISP unit 210 via a connector 224 located on the case of the ISP unit 210. This connector is preferably of type disclosed in Applicant Kuzma's provisional patent application, Ser. No. 60/111,103, filed Dec. 7, 1998, (now a non-provisional application Ser. No. 09/455,046 filed Dec. 6, 1999) incorporated herein by reference. The ISP unit 210 includes an implantable microphone 218 as an integral part thereof. Such microphone is realized by incorporating or mounting a microphone diaphragm 218' in or near the case of the ISP unit 210, and coupling such diaphragm 218' to a suitable transducer element, such as a piezoelectric crystal, as is commonly used in microphones.

The cochlear electrode array 114 may assume any suitable electrode design as is known in the art, such as that shown in U.S. Pat. 4,819,647. A preferred electrode design is as described in U.S. patent application Ser. No. 09/247,734, filed Feb. 9, 1999, now U.S. Pat. No. 6,129,753, which patent is incorporated herein by reference.

Figure 7:
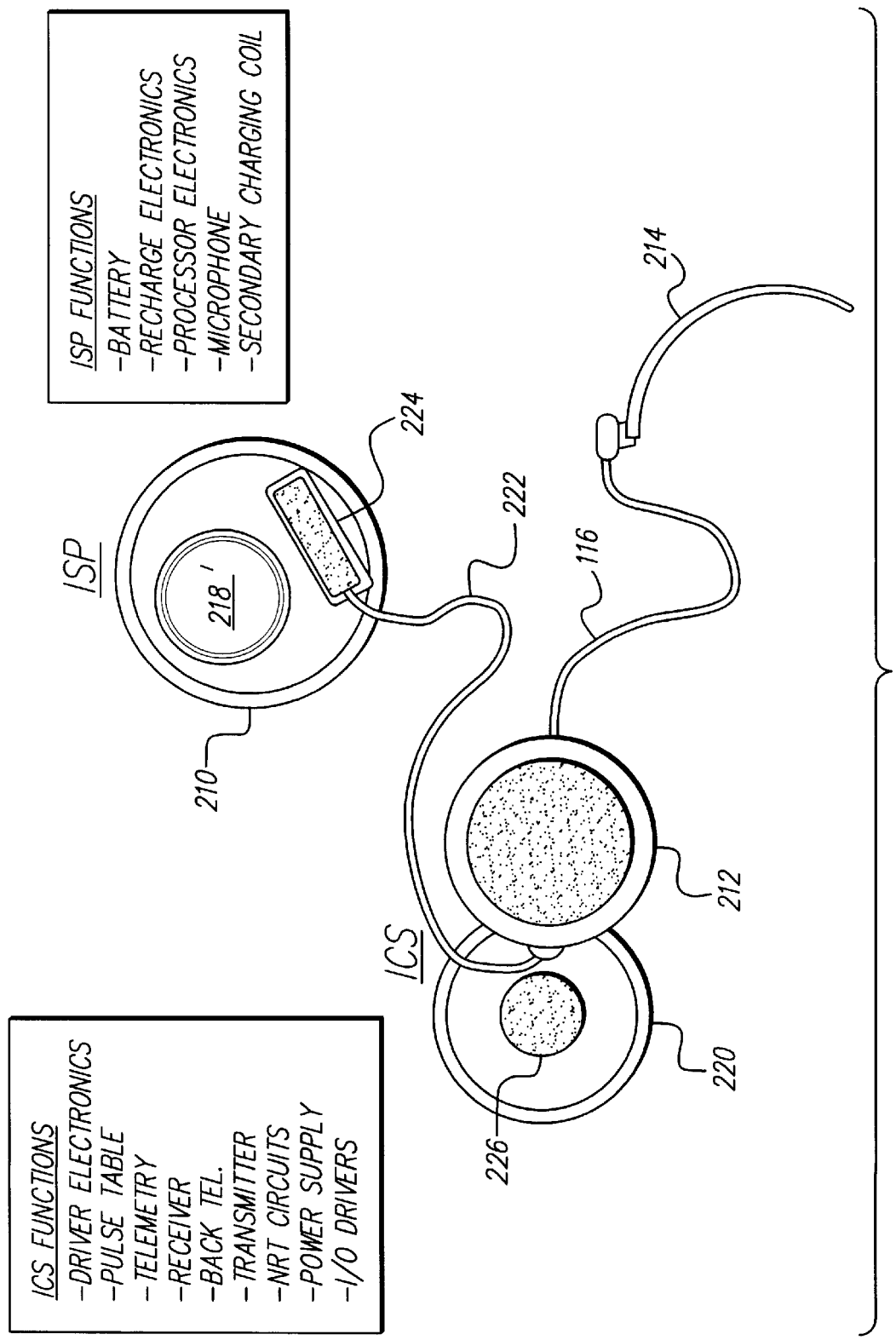
FIG. 7 is a schematic diagram of the preferred, partitioned, wired, cochlear implant system shown in FIG. 6, and further includes additional detail relative to the components of such system.
Figure 8:
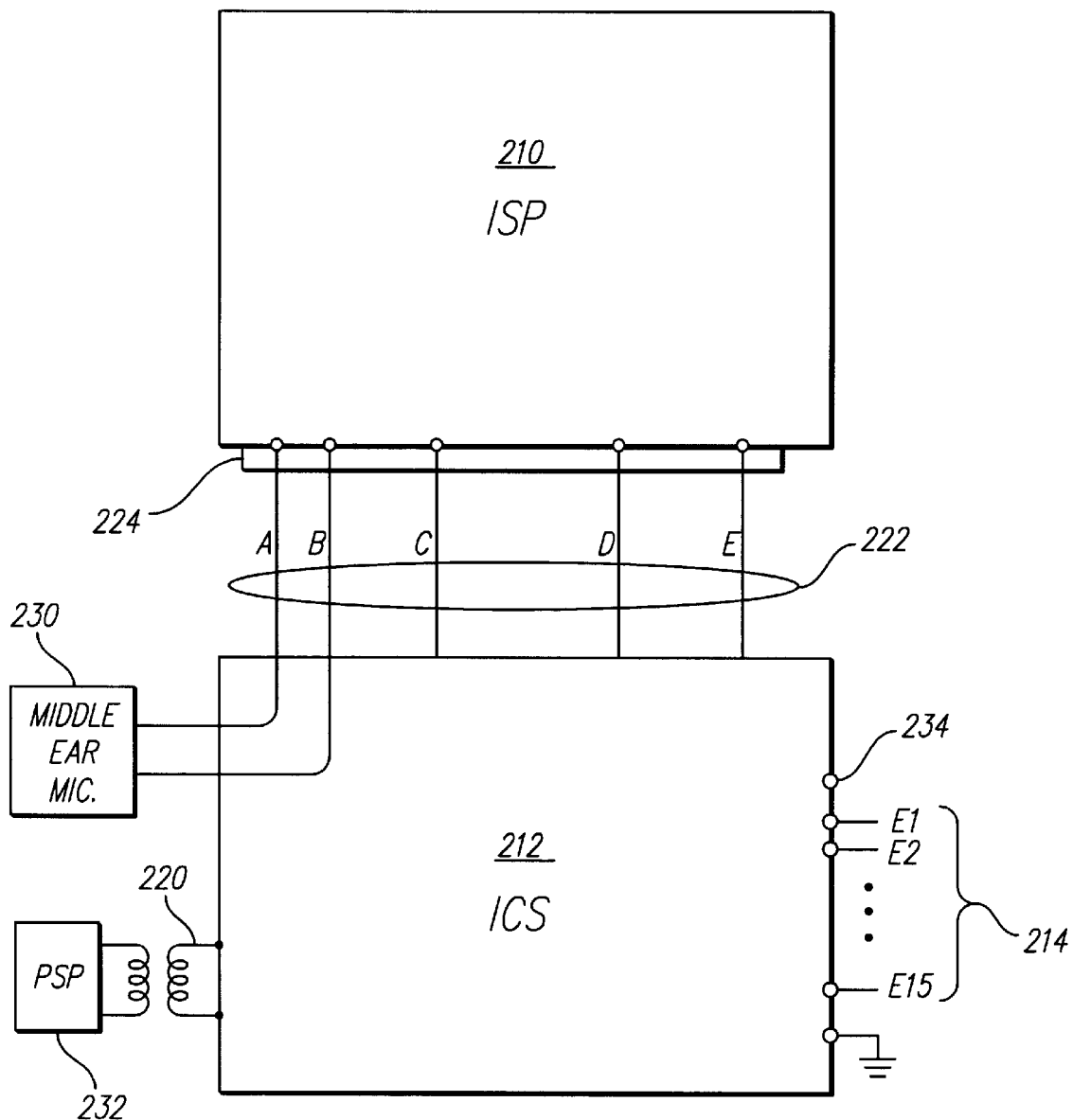
FIG. 8 is a block diagram of the fully implantable system of FIG. 6, and further defines the relationship between FIGS. 8A and 8B.

A more detailed schematic representation of the fully implantable system 170 is presented in FIG. 8. The representation presented in FIG. 8 is more detailed in the sense that additional detail information about the preferred fully implantable cochlear implant system 170 is provided. For example, as seen in FIG. 7, the functions provided by the preferred ICS unit 212 include: (1) driver electronics (circuitry that defines and controls the I/O current sources that apply a prescribed current to each electrode contact of the electrode array 214); (2) a pulse table (a memory element that defines the pulse width, pulse amplitude, and pulse duration, and pulse rate of the stimulation pulses applied to the electrode array 214 as a function of control signals provided thereto from the ISP unit); (3) a telemetry receiver (to receive signals coupled to the system 170 through the coil 220 from an external device); (4) a back telemetry transmitter (to transmit signals through the coil 220 to an external receiver); (5) Neural Response Telemetry (NRT) Circuits (to sense tissue depolarization and other events that are detectable through bioelectrically-generated signals, such as occur in the stapedius muscle tissue in the middle ear); (6) a power supply (to generate the various voltages needed throughout the various circuits within the system 170); and (7) the input/output (I/O) current sources (to generate the currents applied to the electrodes on the electrode array 214).

As also seen in FIG. 7, the functions provided within the ISP unit 210 include: (1) a rechargeable battery; (2) recharging circuitry; (3) speech processing circuitry; (4) a microphone; and (5), in some embodiment, a secondary recharging coil.

Additional details associated with many of the above functions, as well as additional information regarding the operation and programing of a cochlear implant device, may be found in one or more of the following U.S. Patent Applications or Patents, each of which is incorporated herein by reference: (1) "Self-Adjusting Cochlear Implant System and Method for Fitting Same", Ser. No. 09/202,751, filed Dec. 15, 1998, now U.S. Pat. No. 6,157,861; (2) "Multichannel Cochlea Prosthesis With Flexible Control of Stimulus Waveforms", U. S. Pat. No. 5,601,617; (3) "Remote Monitoring of Implantable Cochlear Stimulator", Ser. No. 09/344,429, filed Jun. 25, 1999, now U.S. Pat. No. 6,195,585; (4) "Programmable Current Output Stimulus Stage for Implantable Device", Ser. No. 09/338,700, filed Jun. 23, 1999, now U.S. Pat. No. 6,181,969; and (6) "Strategy Selector for Multichannel Cochlear Prosthesis", Ser. No. 09/322,712, filed May 28, 1999.

As has been previously indicated, and as illustrated in FIG. 8, in a preferred embodiment, the ICS unit 212 is "wired" to the ISP unit 210 via a multi-conductor cable 222 that includes only five conductors. Limiting the number of electrical interconnections between the partitioned units 210 and 212 to a small number is important because each interconnection can be made only at the expense of an electrical feedthrough pin that must pass through the hermetically sealed case of each unit.

Figure 8A:
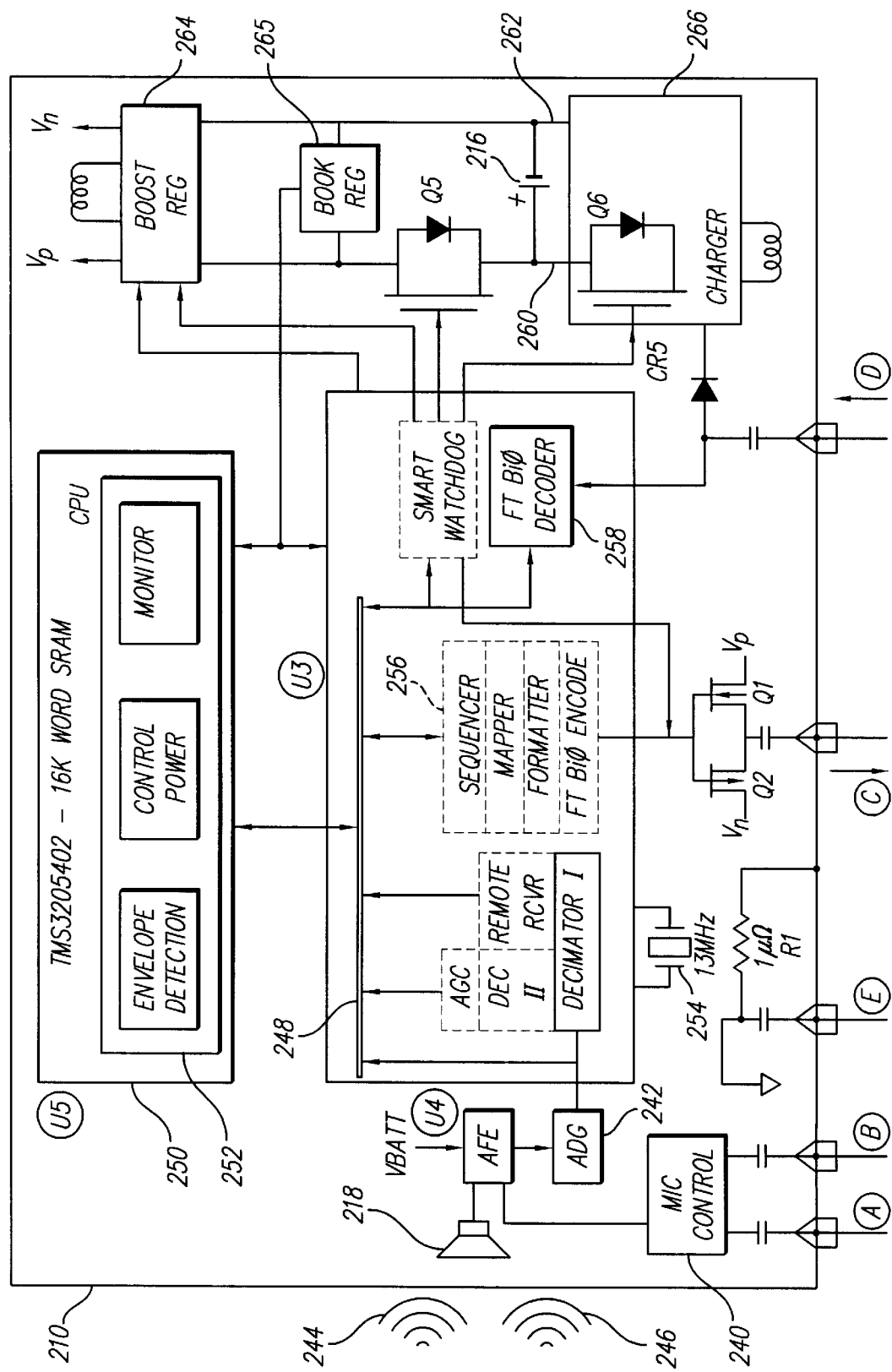
FIG. 8A is a block diagram that depicts the system architecture of the ISP portion of the preferred implant system shown in FIG. 6.
Figure 8B:
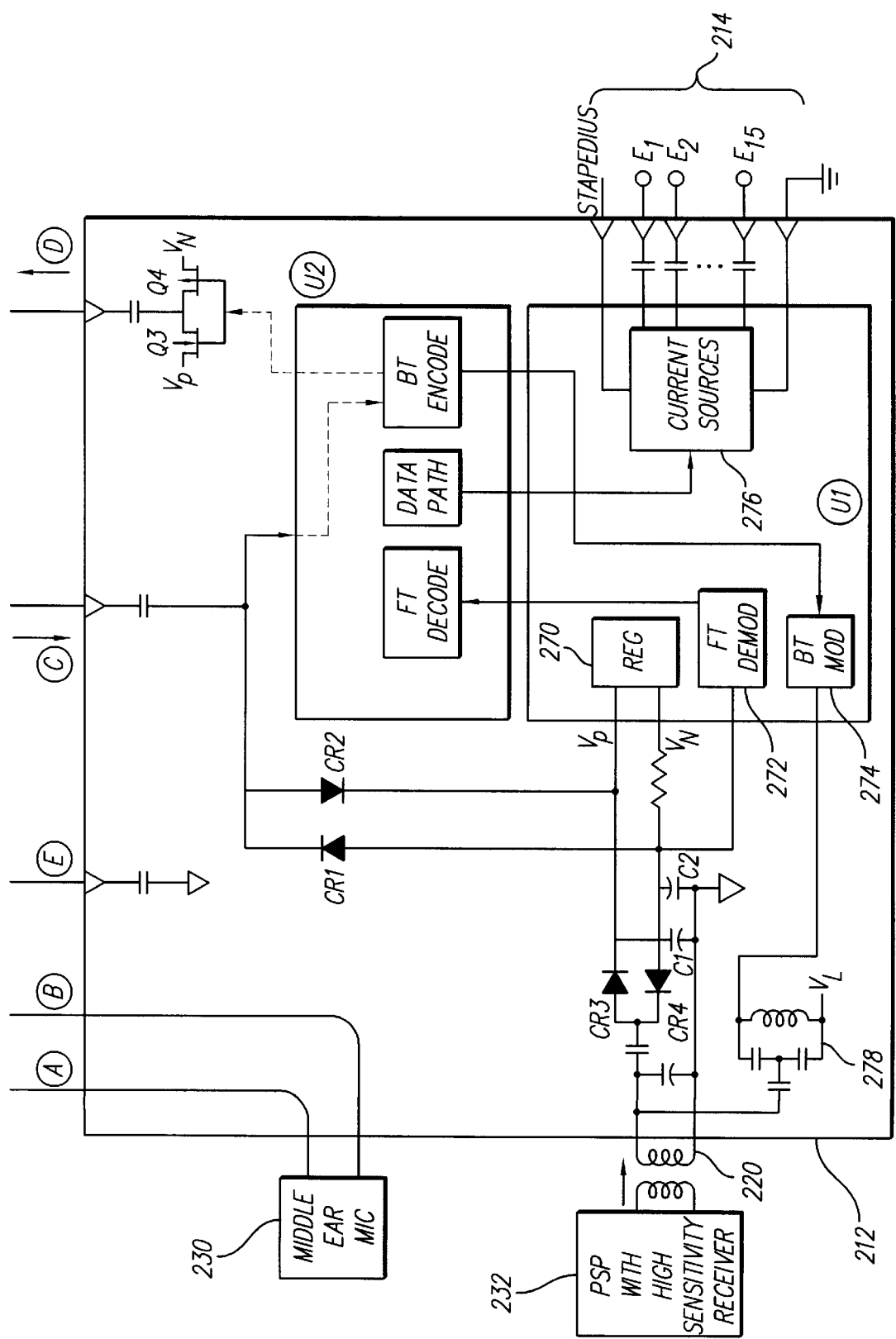
FIG. 8B is a block diagram that depicts the system architecture of the ICS portion of the preferred implant system shown in FIG. 6.

The manner in which the implant system 170 uses only five conductors in the interconnect cable 222 is illustrated in FIGS. 8, 8A and 8B. Actually, as is evident from the description of these figures, only three of those five conductors are needed for interconnections between the ISP unit 210 and ICS unit 212. That is, as seen in FIG. 8, the connector 224 allows five conductors, "A", "B", "C", "D" and "E", to be connected to circuitry within the ISP unit 210. Of these five conductors, two conductors, "A" and "B", are used to connect circuitry within the ISP unit 210 to an external microphone 230. Three conductors, "C", "D"and "E" are used to connect with circuitry within the ICS unit 212.

FIG. 8 further shows that the ISP unit 212 must also provide other feedthrough pin connections in order to make electrical contact with elements of the system that are not included within the hermetically sealed housing of the ICS unit. For example, two feedthrough connections are required for making connection with the coil 220 (which is adapted to be aligned with and receive data and power signals from an external device, such as a low power pocket speech processor (PSP) 232 or an external headpiece 136 (FIG. 1F)). Additionally, sixteen feedthrough connections are required for connection with the electrode array 214. Additionally, if a stapedius electrode 234 is used, an additional feedthrough connection is needed.

FIG. 8A details the circuit architecture that is employed within the ISP unit 210. Similarly, FIG. 8B details the circuit architecture that is employed within the ICS unit 212. These two figures, FIGS. 8A and 8B, when placed adjacent each other, i.e., with FIG. 8A above FIG. 8B, illustrate the complete architecture of the implant system 170. In the discussion that follows, it will be helpful to refer to the two figures, FIGS. 8A and 8B, as though they were one figure.

As seen in FIG. 8A, the ISP unit 210 includes a Lithium-Ion (LIon) battery 216. Such battery is selected because of its charge density and its recharging characteristics. The specifications of such battery 216 are provided hereafter. Other types of batteries, or replenishable power sources (e.g., ultracapacitors), could be used in lieu of, or supplemental to, the LIon battery 216. It is the LIon battery 216 that provides the operating power to both the ISP 210 unit and the ICS unit 212 during a normal mode of operation. However, during other modes of operation, e.g., during a recharging mode, an override mode (where an external speech processor is used to override the ISP 210), a boosting mode (where an external battery is used to supplement or "boost" the power provided from the implanted battery 216), or a fitting/diagnostics or programming mode, power and/or control signals is/are received through the coil 220 attached to the ICS unit 212.

During normal operation, as evident from FIG. 8A, the battery 216 resides between two voltage rails 260 (positive rail) and 262 (negative rail). A voltage boost regulator circuit 264 resides between these two rails and provides the primarily operating voltages $V_P$ (positive) and $V_N$ (negative) for the remaining circuitry. The voltage regulator circuit 264 may be obtained commercially as device number LT1613 from Linear Technologies. A separate regulator circuit 265, referred to as the buck regulator, helps provide the needed operating voltages for the TMS3205402 processor and U3 gate array. This separate regulator may be realized using a LT1627 regulator circuit, available commercially from Linear Technology Corporation. Linear Technology Corporation can be contacted at the internet web address of www.linear-tech.com.

Except where indicated, the regulated voltages $V_P$ and $V_N$ are used throughout the ISP circuits and ICS circuits. These voltages are further transferred from the ISP unit 210 to the ICS unit 212 over conductors "C" and "E" (where conductor "E" functions as the reference, or ground). As seen in FIG. 8A, two transistors, Q1 and Q2, operate to amplify and switch (i.e., buffer) the voltage on conductor "C" between $V_P$ and $V_N$, as controlled by modulation data obtained from circuit U3. Hence, in this manner an ac voltage is present on conductor "C" that has, relative to the reference (or ground) conductor "E", positive and negative peak values of $V_P$ and $V_N$, respectively. On the ICS side of conductors "C" and "E", the ac VP-VN signal is rectified and filtered through diodes CR1 and CR2 and capacitors C1 and C2 to provide similar regulated voltages $V_P$ and $V_N$ within the ICS unit 212. Data is stripped from the ac signal by way of demodulator circuit 272 within the gate array U1 of the ICS unit 212.

During modes other than a normal operation, i.e., when operating power is supplied from an external source, an ac signal is received through coil 220, and then rectified and filtered through diodes CR3 and CR4 and capacitors C1 and C2, to provide voltages $V_P$ and $V_N$ within the ICS unit 212. These voltages are then switched by switching transistors Q3 and Q4 to create an ac signal that is applied to conductors "D" and "E" (where "E" is the reference or ground) and sent to the ISP unit 210. On the ISP side, such ac signal is applied to a charging circuit 266, through diode CR5, which charging circuit 266 rectifies the ac-signal and applies appropriate dc voltages to the positive and negative voltage rails 260 and 262, thereby allowing the battery 216 to be charged. The charging circuit may be obtained commercially as device number LT1510 from Linear Technology Corporation.

As shown in FIG. 8A, the ISP unit 210 includes an analog front end (AFE) circuit U4 that is coupled to internal microphone 218. Also connected to the AFE chip U4 is a microphone control circuit 240 that is connected, through respective coupling capacitors and feedthrough pins, with the conductors "A" and "B" that connect with the external (middle ear) microphone 230. The conductors "A" and "B" are shown in FIG. 8 (and FIG. 8B) as passing over the ICS unit 212. This simply means that, in practice, these two wires, "A" and "B", may be bundled in or with the same lead 216 that is used to connect with the electrode array 214.

As further seen in FIG. 8A, the AFE circuit U4 is connected to an analog-to-digital converter (ADC) circuit 242. The ADC circuit 242, in turn, connects with a gate array chip U3. The gate array chip U3, in combination with processor chip U5, performs many digital logic functions, as seen in FIG. 8A. One of the functions is to process the signal received through the AFE chip signal path. Such received signal may comprise either a "speech" signal 244, or an acoustic control signal 246 generated by an acoustic remote control. The processing of such signal typically includes processing in a first decimator circuit, DECIMATOR I (a decimator circuit converts two samples into one sample), processing in a second decimator circuit, DECIMATOR II (processing in two decimator circuits effectively converts four samples into one sample), and subjection to an automatic gain control (AGC) circuit. Some received signals, e.g., control signals from the acoustic remote control, after being subjected to the DECIMATOR I processing, are processed through a remote receiver. All such processed signals, including output signals from the ADC circuit 242, may be applied to a data bus 248.

The data bus 248 allows data to be sent to, and received from, processor chip circuit U5. Included within processor U5 is at least 16 KWords of memory, realized using static random access memory (SRAM) circuits. The memory circuits 250 included as part of U5, or other memory circuits, store data relating to envelope detection, power control, and other monitoring functions. The processor chip U5 is realized using a TMS320–5402 processor chip commercially available from Texas Instruments (TI). Texas Instruments can be contacted at the internet web address of www.ti.com. Such processor chip U5 includes a basic CPU 252 as an integral part thereof to facilitate the data processing and control that occur during operation of the cochlear implant system.

A 13 MHz crystal 254 provides a stable clock base for operation of the gate array chip U3 and processing chip U5, and other processing that occurs within the ISP 210.

The conductor "E", one of the five conductors that passes through the connector 224, provides a ground reference connection between the ISP unit 210 and the ICS unit 212. In order to avoid any possibility of dc current flow between the two units, the ground reference conductor "E" is capacitively coupled at each feedthrough pin. Additionally, a large resistor R1, e.g,. a 1M ohm resistor, connects the capacitor used in such coupling to the case of the ISP unit, as well as to ISP ground, in order to prevent charge build-up on the capacitor.

The conductor "C", as has previously been indicated, is used primarily to send power and data from the ISP 210 to the ICS 212. Data signals are generated by modulating an ac signal that switches between two voltage references, $V_N$ and $V_P$, by amplifier/buffering transistors Q1 and Q2. The modulating data, controlled by the gate array chip U4, may first be processed through a sequencer, a mapper, a formatter, and a front-telemetry (FT) biphasic (BiØ) encoder.

Additional functions performed within the DSP chip U3 include that of a smart watchdog circuit 256 and a back telemetry (BT) biphasic (biØ) decoder circuit 258. The watchdog circuit 256 monitors numerous activities and events within the system and takes appropriate shut down action if any goes wrong. For example, if something is not correct, e.g., a monitored voltage is too high or too low, the watchdog circuit may disconnect the battery 216 through transistor switch Q6, disconnect the ISP-supplied power through transistor switch Q5, and/or (3) disable the boost regulator 264.

The ICS unit 212 includes an analog chip U1 and a gate array chip U2. The analog chip U1 includes circuits that provide: (1) voltage regulation of voltages $V_P$ and $V_N$ in a voltage regulator circuit 270; (2) forward-telemetry demodulation of any data signals received through the coil 220 in an FT Demodulation circuit 272; (3) back-telemetry modulation of any data to be transmitted through the coil 220 in a BT Modulator circuit 274; and (4) programmable currents that drive the sixteen electrodes included in the electrode array 214 through programmable current sources 276. A transmitter circuit 278 applies the modulated BT data to the coil 220 so that it can be received externally, e.g., through a PSP unit 232.

The gate array chip U2 performs most of the digital signal processing needed within the ICS unit 212. Such processing includes forward telemetry decoding, defining the data path for the signals being applied to the electrodes of the electrode array, and encoding of the back-telemetry data.

As described in FIGS. 8, 8A and 8B, it is thus seen that a fully implantable, compact, partitioned, "wired" embodiment of the cochlear implant system is provided that requires only a minimum number of conductors within the multi-conductor cable 222 that interconnects the ICS unit 212 with the ISP unit Turning next to FIGS. 9A and 9B, a plan and side cross-sectional respectively, is shown of the preferred mechanical packaging of the ISP unit 210.

From the plan view, FIG. 9A, the ISP unit 210 appears as a round disk, and has a diameter of approximately 32 to 36 mm. From the side cross-sectional view, FIG. 9B, it is seen that the ISP unit 210 has a depth, P, where P is about 8.4 mm. The unit 210 is made from two clamshell metal halves 302 and 304, joined together at their edges with an hermetically sealed weld 310. These metal halves 302 and 304 are made from a suitable metal, e.g., titanium, stainless steel, or the like, which metals are compatible with body tissue. An electrical feedthrough pin 306, which is part of the connector 224, provides an electrical connection through the metal shell 304 to the inside of the metal can formed by the two clamshell halves 302 and 304.

The battery 216 is preferably rectangular in shape and fills a substantial portion of the volume within the case or can formed by the two metal clamshells 302 and 304. The microphone diaphragm 218' resides against a recess made in the clamshell half 304. The inside surface of the clamshell 304 is mechanically coupled, via support plate 223 and shaft member 221, to a microphone transducer 219. The diaphragm 218', plate 223, shaft member 221, and transducer 219 cooperatively function together to form the implanted microphone 218 (FIG. 1F). The volume inside the ISP case not occupied by the battery 216 and microphone 218 is generally occupied with the electronic circuitry associated with the ISP circuit functions (See FIG. 8A).

Figure 10A:
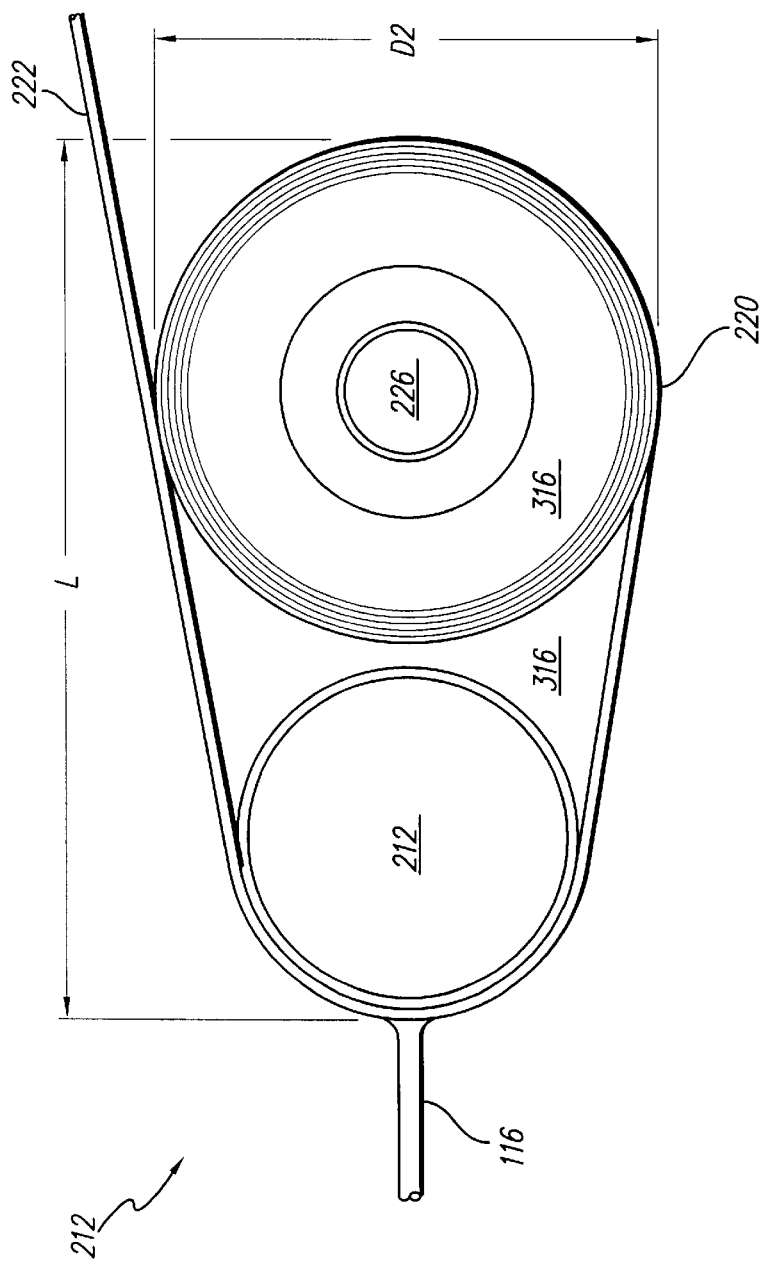
FIGS. 10A and 10B are similarly a plan and side view, respectively, illustrating the preferred mechanical packaging of the ICS used in the system shown in FIG. 6.
Figure 10B:
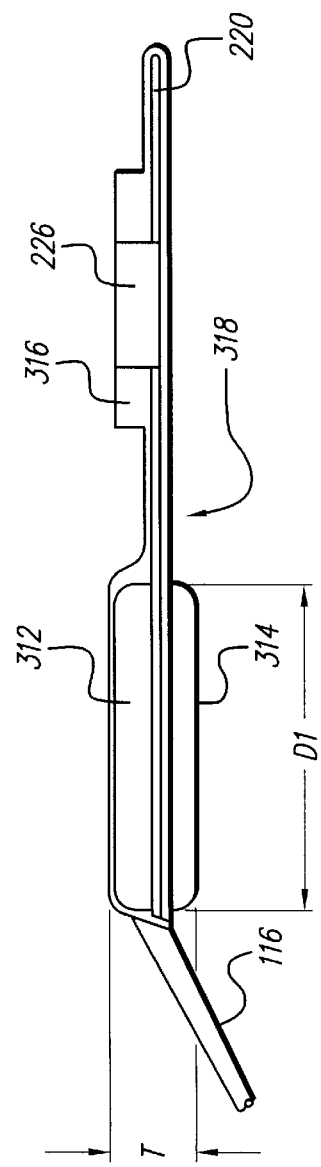

FIGS. 10A and 10B similarly show a plan and side view, respectively, of the preferred mechanical packaging of the ICS unit 212 used in the system shown in FIG. 6. As seen in these figures, the coil 220 is positioned adjacent the ICS 212. The two wires from the coil 220, as well as the conductors within the cable 222 (going to the ISP 210), and the wires within the cable 116 (going to the electrode array 114) all tangentially attach to the case of the ICS 212 around its perimeter. The ICS unit 212 is made from two clamshell metal halves 312 and 314 which are hermetically welded together around their rim. The upper clamshell 312, as well as the coil 220, and magnet 226 are all embedded in a silicone rubber encapsulant 316. Such encapsulant 316 is flexible, thereby allowing the coil/magnet assembly 220/226 to bend to some extent at flexure point 318. This flexure facilitates positioning the ICS unit 212 and coil/magnet assembly flat against a curved skull bone.

As seen in FIG. 10B, the diameter, D1, of the case of the ICS unit 212 (which case is made from clamshells 314 and 312) is about 20 mm. Some embodiments may be smaller. The thickness, T, of the ICS can is about 5.2 mm. As seen in FIG. 10A, the diameter, D2, of the coil 220 is about 32 mm. The overall length, L, of the ICS assembly, including the coil 220, is about 55 mm. The clamshell halves 312 and 314 of the ICS unit 212 may be made from the same metals as are the clamshell halves 302 and 304 of the ISP unit 210, e.g., titanium, or an alloy of titanium, or stainless steel. The length of the lead 222 is preferably about 60 mm.

The dimensions presented above for various components of the system may vary depending on system options and selected system components. For example, current technology dictates that a battery of the size indicated in FIGS. 9A and 9B be employed in order to provide the operating life and other parameters desired. However, future battery technology (or other power source technology) may allow future revisions of the ISP to be made smaller.

Thus, it is seen that a fully implantable cochlear implant system has been described. Such system is realized using two implantable separately packaged devices, an ISP unit 210 and an ICS unit 212. The implantable devices are designed so that the same device set can be used on either the left or right side of the head. The ICS unit 212 provides a function that is the same as or similar to current implantable cochlear stimulators. Advantageously, the ICS unit 212 may operate without being "wired" to the ISP 210 using a conventional external processor, e.g., a PSP processor 232. Hence, should ISP unit malfunction, or should its battery go dead, or for other reasons, the patient can still use the ICS unit as long as it is coupled in conventional manner (through coil 220) with an external controller.

It is noted that the coil 220 is located outside of the hermetic package of the ICS unit 212. Such location facilitates the efficiency with which RF and magnetic signals can be coupled thereto or therefrom. During selected operating modes, the coil 220 is used to provide power for operation, power for recharging, forward data telemetry signals, and back telemetry RF signals.

One advantage of having the magnet 226 located in the center of the coil 220 is that the magnet 226 can be removed surgically, if needed, to allow an MRI exam to take place. After the MRI exam is completed, the magnet can be readily surgically inserted back into its slot within the encapsulant material 316 that holds the coil/magnet assembly in place.

The back telemetry features of the implant system advantageously allow a back telemetry signal to be transmitted to a remote device that provides evoked potential data, stapedius electrode data, microphone test data, operating power data, various test signals for system test, and miscellaneous other data signals useful in the operation and diagnostic evaluation of the system.

The ISP 210, as described above, includes speech processor electronics, a battery, recharging electronic circuits, and a subcutaneous microphone, all located inside of an hermetic implantable housing. The connector 224 provides five physical connections for power, telemetry, and microphone signals.

As required, an external speech processor, e.g., a belt-worn unit, may provide stand-alone operation of the ICS unit 212 when the implanted battery becomes discharged or if the ISP unit 210 fails to operate correctly. The external speech processor may also provide a slow charge to the implanted battery, and provides auxiliary power to operate the implanted ICS unit 212 during recharge periods. Additionally, the external speech processor may be fitted with an extra capacity battery to support simultaneous operation and charging.

The external speech processor operating time when used for charging and hearing is at least 5 hours. This assumes a requirement to replenish 40% of a 600 mwhr battery charge, at a transfer efficiency of at least 30%. Under the same assumed conditions, the speech processor operating time when used for hearing support only is at least 30 hours.

The battery 216 is selected to provide at least 50 hours of continuous operation between recharge cycles after four years of implanted use.

Control of volume, sensitivity, program selection, auxiliary mode selection, and other user adjustable features is accomplished by downloading adjustment parameters from an external speech processor during a programming mode of operation. Additionally, an acoustic remote control may be used to allow user control of at least some of these functions.

An MRI-compatible patient-accessible emergency cut-off switch is provided as part of the system that causes both the ICS unit 212 and the ISP unit 210 to stop operation in the event that effective operation cannot be controlled using conventional methods. The purpose of this cut-off switch is to sop device operation when stimulation becomes uncomfortable or unsafe. A start-up sequence is also provided that allows for the use of a transcutaneous bi-directional telemetry link to support diagnostics while the stimulation function is disabled.

Several modes of operation of the implant system are possible, as indicated below:

(1) A program and fitting mode of operation is invoked when the system is being fitted to the patient with operating and charging power being provided by the external fitting system.

(2) A normal operation mode is used then the implanted system is providing hearing stimulation and is operating from its own implanted power source.

(3) A base station recharge with internal operation mode is used when the implanted system is operating normally at the same time that an external base station is providing operating power and recharge power.

(4) A body worn recharge, power assist and internal operation mode is used when the implanted system is operating normally while a mobile body worn power source, e.g., a PSP 232 (FIG. 8), provides operating power and recharge power.

(5) A body worn recharge and external operation mode is used when the implanted ISP unit 210 is deactivated with an external body-worn speech processor, e.g., a PSP 232, which body-worn speech processor provides speech processing, recharging and operating power for the ICS unit 212.

(6) A system test and diagnostic mode is used where the external fitting or test system provides all operational and recharge power, and wherein such external devices support two-way data communication.

(7) A sleep mode, or low power mode, is used that provides a minimal level of hearing sensation for use during periods of low activity and/or rest.

The implant system is designed to consume between 7 to 30 mW of power during normal operation, depending on the stimulation mode (depending upon the particular speech processing strategy that is selected). The battery 216 housed within the ISP unit 210 comprises a LIon battery having a power density of approximately 240 mWhr/cc. The voltage provided by the battery 216 is 3.6 volts average during a discharge cycle. The total capacity of the battery is at least 400 mWhr. The number of discharge/recharge cycles that the battery may experience is at least 1000 for a 50% discharge with daily recharging. The dimensions of the battery are approximately 16.4 mm by 5.6 mm by 25 mm. The volume of the battery is about 2.52 cc.

Although the present invention has been described in terms of a cochlear implant device, and while certain features of the invention are particularly suitable for use in a cochlear implant device, it is to be emphasized that the fully implantable partitioned features of the invention (e.g., partitioning various functions into separate coupled implanted packages) may be applied to other implantable neural or muscular stimulation devices, or other implantable devices.

Thus, while the invention herein disclosed has been described by means of specific embodiments and applications thereof, numerous modifications and variations could be made thereto by those skilled in the art without departing from the scope of the invention set forth in the claims.

What is claimed is:

1. A fully implantable cochlear implant system, comprising:
    an implantable, hermetically-sealed, cochlear stimulator (ICS) unit (212), the ICS unit having electrical circuitry therein;
    an implantable, hermetically-sealed speech processor (ISP) unit (210), the ISP unit having processing circuitry therein, the ISP unit further having a case on which a connector is mounted, the connector having a plurality of feedthrough terminals through which electrical contact may be made with the processing circuitry located inside of the ISP unit;
    a power source (216) housed within the ISP unit for providing operating power for the cochlear implant system;
    a cochlear electrode array (114) permanently connected to the ICS unit via a first multi-conductor cable (116) and adapted to be insertable into a human cochlea;
    a second multi-conductor cable (222) having a first end permanently connected to the ICS unit, and having a second end detachably connected to the ISP unit through the connector mounted to the ISP case, whereby the ISP unit is wired to the ICS unit; and
    a subcutaneous microphone (218);
    wherein microphone signals sensed by the microphone are processed by the processing circuitry within the ISP unit, and stimulation signals representative of the sensed microphone signals are coupled to the electrical circuitry within the ICS unit, and wherein the electrical circuitry within the ICS unit responds to the received stimulation signals and generates stimulation pulses that are sent to the electrode array through the first cable for the purpose of electrically stimulating cochlear tissue in the vicinity of the array.

2. The fully implantable system of claim 1 further including a coil (220) permanently connected to the ICS unit through which electrical data signals may be received from an external source.

3. The fully implantable system of claim 2 wherein the power source comprises a rechargeable battery, and wherein the processing circuitry within the ISP unit includes recharging circuits, and further wherein power signals for recharging the battery are received through the coil during a recharging mode of operation.

4. The fully implantable system of claim 3 wherein the rechargeable battery comprises a Lithium Ion battery having a power density of at least 240 mWhr/cc.

5. The fully implantable system of claim 3 wherein power signals received through the coil during a programming mode of operation provide operating power for the system.

6. The fully implantable system of claim 3 wherein power signals received through the coil during a diagnostic testing mode of operation provide operating power for the system.

7. The fully implantable system of claim 3 wherein power signals received through the coil are modulated with programming data to provide programmed control of the system, whereby the ICS unit may operate independent of the ISP unit as controlled by power signals and programming data received through the coil.

8. The fully implantable system of claim 1 wherein the subcutaneous microphone includes a microphone diaphragm (218') that is integral with the case of the ISP unit.

9. The fully implantable system of claim 1 wherein the second multi-conductor cable 222 contains only five conductors.

10. The fully implantable system of claim 9 further including a supplemental microphone, and wherein two of the five conductors within the second multi-conductor cable connect to the supplemental microphone.

11. The fully implantable system of claim 9 wherein three of the five conductors within the second multi-conductor cable connect with the electrical circuitry within the ICS unit, wherein a first of these three conductors is used as a ground reference, a second of these three conductors is used, in combination with the ground reference conductor, to transfer power and data from the ICS unit to the ISP unit, and a third of these three conductors is used, in combination with the ground reference conductor, to transfer power and data from the ISP unit to the ICS unit.

12. The fully implantable system of claim 11 wherein each of the three conductors used to connect the ISP unit to the ICS unit are capacitively coupled, whereby dc current may not flow between the ICS and ISP units.

13. A fully implantable system comprising two implantable units, each unit having electrical circuitry therein that in combination performs a desired implant function, one of the units having a power source therein, one of the units having a coil attached thereto through which external power and control signals may be received; one of the units having an electrode attached thereto through which stimulation or sensing functions may be performed; and a detachable cable electrically connecting the two units so that the power and data signals originating in one of the units may be shared with the other unit.

14. The fully implantable system of claim 13 wherein power signals received through the coil provide operating power for the system, and the power source included in one of the units does not provide operating power.

15. The fully implantable system of claim 13 wherein the power source comprises a rechargeable battery, and further wherein power signals received through the coil recharge the battery.

16. The fully implantable system of claim 15 wherein the power signals received through the coil are modulated with control data, and wherein the control data, when received, is used to control the operation of the implant function.

17. The fully implantable system of claim 15 wherein the circuit functions provided in each of the units is partitioned so that a first of the units contains circuitry essential to carrying out the intended implant function and includes the coil attached thereto, and a second of the units contains circuitry for managing the implant function and further includes the rechargeable power source; wherein the first unit may operate independent of the second unit when power signals and control data are received through the coil.

18. The fully implantable system of claim 17 wherein the first unit comprises an implantable cochlear stimulator (ICS), and the second unit comprises an implantable speech processor (ISP), and wherein a cochlear electrode array is attached to the ICS and a telemetry coil is attached to the ICS, and further wherein a rechargeable battery is carried in the ISP and a subcutaneous microphone is coupled to the ISP; wherein during a normal mode of operation all of the functions of a cochlear stimulation system are provided through the ICS and ISP units; and further wherein during other modes of operation, the power and speech processing functions carried out by the ISP may be replaced by an external speech processor that is coupled with the coil of the ICS.

19. A method of providing a fully implantable stimulation system comprising:

(a) partitioning the functions of the stimulation system into a plurality of functional groups;

(b) placing electrical circuitry associated with each functional group into separate, implantable, hermetically sealed cases;

(c) placing a power source in one of the implantable cases;

(d) attaching an antenna coil to another one of the implantable cases, wherein the antenna coil is adapted to receive power and data signals from a remote source;

(e) attaching a means for delivering stimulating pulses to body tissue to one of the implantable cases;

(f) implanting each of the implantable cases; and (g) electrically coupling each of the implantable cases to at least one other of the implantable cases so that power and data may be shared between the electrical circuitry contained within the respective implantable cases;

whereby the circuitry and system components contained in or attached to each of the implantable cases combine to provide the desired implant function, thereby providing a fully implantable simulation system.

20. The method of claim 19 wherein step (a) comprises partitioning the functions of the stimulation system into essential functions and administrative and control functions; wherein step (b) comprises placing the circuitry responsible for carrying out the essential functions into a first implantable case, and placing the circuitry responsible for carrying out the administrative and control functions into a second implantable case; wherein step (c) comprises placing the battery in the second implantable case; wherein step (d) comprises attaching the coil to the first implantable case; and wherein step (e) comprises attaching the means for delivering stimulating pulses to the first implantable case; whereby the first implantable case may operate independently from the second implantable case when administrative, control and power signals are provided to the first implantable case through the coil attached to the first case.

* * * * *